United States Patent
Schiene-Fischer et al.

(10) Patent No.: US 7,589,065 B2
(45) Date of Patent: Sep. 15, 2009

(54) CATALYSIS OF THE CIS/TRANS-ISOMERISATION OF SECONDARY AMIDE PEPTIDE COMPOUNDS

(75) Inventors: Cordelia Schiene-Fischer, Halle (DE); Gunter Fischer, Halle (DE); Judith Maria Habazettl, Richen (CH); Gerhard Küllertz, Halle (DE)

(73) Assignee: Max-Planck Gesellschaft zur Forderung der Wissenschaften, C.V., Berlin (DE)

( * ) Notice: Subject to any disclaimer, the term of this patent is extended or adjusted under 35 U.S.C. 154(b) by 430 days.

(21) Appl. No.: 10/487,750

(22) PCT Filed: Aug. 20, 2002

(86) PCT No.: PCT/EP02/09300

§ 371 (c)(1),
(2), (4) Date: Sep. 29, 2004

(87) PCT Pub. No.: WO03/018618

PCT Pub. Date: Mar. 6, 2003

(65) Prior Publication Data

US 2005/0043213 A1 Feb. 24, 2005
US 2006/0100130 A9 May 11, 2006

(30) Foreign Application Priority Data

Aug. 20, 2001 (DE) .............................. 101 40 777

(51) Int. Cl.
*A61K 31/16* (2006.01)
*A61K 38/05* (2006.01)
*C07C 233/31* (2006.01)
*C07K 5/06* (2006.01)

(52) U.S. Cl. ........................... 514/19; 514/616; 554/56
(58) Field of Classification Search .................. None
See application file for complete search history.

(56) References Cited

U.S. PATENT DOCUMENTS

| | | | | |
|---|---|---|---|---|
| 5,266,576 | A | | 11/1993 | Vincent et al. .............. 514/300 |
| 5,412,125 | A | * | 5/1995 | Philippe ...................... 554/35 |
| 5,559,092 | A | * | 9/1996 | Gibson et al. .................. 514/2 |
| 5,843,960 | A | * | 12/1998 | Steiner et al. ............... 514/317 |
| 6,043,341 | A | * | 3/2000 | Udodong et al. ............ 530/317 |
| 6,316,405 | B1 | * | 11/2001 | Rich et al. ...................... 514/9 |
| 6,462,173 | B1 | * | 10/2002 | Lu et al. ..................... 530/328 |

FOREIGN PATENT DOCUMENTS

| | | |
|---|---|---|
| JP | 1294800 A | 5/1988 |
| WO | WO98/30535 | 7/1998 |

OTHER PUBLICATIONS

Kragol et al. The Antibacterial Peptide Pyrrhocoricin Inhibits the ATPase Actions of DnaK and Prevents Chaperone-Assisted Protein Folding. Biochemistry. Feb. 10, 2001, vol. 40. No. 10, pp. 3016-3026.*
Otvos, Jr. et al. Insect peptides with improved protease-resistance protect mice against bacterial infection. Protein Science. 2000, vol. 9, pp. 742-749.*
1 PG, "Catalogue Bachem Peptides and Biochemicals Germany," Bachem Biochemica GmbH, 1999.
6 PGS, "The hsp70 chaperone DnaK is a secondary amide peptide bond *cis-trans* isomerase," Schiene-Fischer et al., Nature Structural Biology, vol. 9, No. 6, Jun. 2002.
8 PGS, "Inhibition of the $Na^+/H^+$ Exchanger Confers Greater Cardioprotection Against 90 Minutes of Myocardial Ischemia Than Ischemic Preconditioning in Dogs," Gumina et al., Basic Science Reports, Circulation, 1999; 100: 2519-2526.
7 PGS, "Modulation of Substrate Specificity of the DnaK Chaperone by Alteration of a Hydrophobic Arch," Rüdiger et al., J. Mol. Biol. (2000) 304, 245-251.
9 PGS, "Molecular Basis for Interactions of the DnaK Chaperone with Substrates," Biol. Chem., vol. 381, 877-885, Sep./Oct. 2000.
6 PGS, "Structure-Based Design and Synthesis of Novel Thrombin Inhibitors Based on Phosphinic Peptide Mimetics," Li et al., Bioorganic & Medicinal Chemistry Letters 9 (1999) 1957-1962.
7 PGS, "Substrate specificity of the DnaK chaperone determined by screening cellulose-bound peptide libraries," Rüdiger et al., The EMBO Journal, vol. 16, No. 7, 1501-1507, 1997.
5 PGS, "Synthesis, Stability, and Biological Evaluation of Water-Soluable Prodrugs of a New Echinocandin Lipopeptide. Discovery of a Potential Clinical Agent for the Treatment of Systemic Candidiasis and *Pneumocystic carinii* Pneumonia (PCP)," Balkovec et al., Journal of Medicinal Chemistry, 1992, vol. 35, No. 1.
18 PGS, "Tetrahydrofuran as a Scaffold for Peptidomimetics. Application to the Design and Synthesis of Conformationally Constrained Metalloproteinase Inhibitors," Hanessian et al., Tetrahedron 56 (2000) 7643-7660.

* cited by examiner

*Primary Examiner*—Jeffrey E Russel
(74) *Attorney, Agent, or Firm*—Kagan Binder, PLLC

(57) ABSTRACT

The present invention is based on the finding that the cis/trans isomerisation of secondary amide peptide bonds in oligo- and polypeptides can be catalytically promoted. This catalysis is effected by enzymes which are hereinafter called "secondary amide peptide bond cis/trans isomerases (APIases). It can be assumed that the APIase activity plays a central role in a number of pathophysiological processes. Thus, the invention relates to pharmaceutical compositions comprising substances which inhibit APIase activity.

4 Claims, 10 Drawing Sheets

Fig.1: Cis/trans isomerisation of the substrate Ala-Leu after leap of the pH value from 2 to 7.6 (explanation cf. Example 1)

Fig. 2: Dependency of the rate ($k_{obs}$) in the cis/trans isomerisation of the substrate Ala-Leu from the concentration of Dnak (explanation cf. Example 2)

Fig. 3: Dependency of the size of the difference in measurement (amplitudes) between absorption at the time t=0 and absorption after adjustment of the cis/trans equilibrium, plotted at different Dnak concentrations (explanation cf. Example 2)

Fig. 4: Dependency of the rate constant of the cis/trans isomerisation of the substrate Ala-Leu from the Cyp18 concentration (explanation cf. Example 3)

Fig..5: Dependency of the size of the difference in measurement (amplitudes) between absorption at the time t=0 and adsorption after adjustment of the cis/trans equilibrium, plotted at different Cyp18 concentrations. (explanation cf. Example 3)

Fig. 6: Determination of the peptidyl-prolyl cis/trans isomerisation rate of the substrate Suc-Ala-Phe-Pro-Phe-NHNp by means of isomer-specific proteolysis depending on the amounts of Dnak added.(explanation cf. Example 5)

Fig. 7: alanine-methyl region of a 2D exchange $^1$H NMR-spectrum for the substrate Ala-Ala-Tyr-Ala-Ala (explanation cf. Example 8)

Fig. 8: alanine-methyl region of a 2D exchange $^1$H NMR-spectrum for the substrate Ala-Ala-Tyr-Ala-Ala in Fig. 7 with addition of catalytic amounts of APIase (explanation cf. Example 8)

CATALYSIS OF THE CIS/TRANS-ISOMERISATION OF SECONDARY AMIDE PEPTIDE COMPOUNDS

DESCRIPTION OF THE INVENTION

The present invention is based on the finding that the cis/trans isomerisation of secondary amide peptide bonds in oligo- and polypeptides can be catalytically promoted. This catalysis is affected by enzymes which are hereinafter called "secondary amide peptide bond cis/trans isomerases (APIases). It can be assumed that the APIase activity plays a central role in a number of pathophysiological processes. Thus, the invention relates to pharmaceutical compositions comprising substances which inhibit APIase activity.

It is well-known that in oligo- and polypeptides the rotation around the bond, which is usually defined by the dieder angle omega ($\omega$) and which is located between the carbonyl C atom and the nitrogen atom, as opposed to other C—N bonds e.g. in aliphatic dialkylamines, is hindered. The description from the field of quantum chemistry furnishes a picture which can be described by the formation of a partial CN double bond (e.g. L. Stryer, Biochemistry, ISBN 3-89330-690-0). Moreover, further rotations around the bonds which are less hindered and which are usually described by the angles psi ($\psi$) and phi ($\phi$) are possible in the backbone of the peptide. The proportions of these angles in the polypeptide chain essentially define the three-dimensional structure of peptides or proteins. These facts are known to the person skilled in the art and can, presently, be measured either directly by NMR-spectroscopy or X-ray structural analysis and can also be predicted and shown by means of three-dimensional contour diagram, the Ramachandran plots, (Ramachandran, et al., 1968, Adv. Prot. Chem., 23:283-437).

The formation of defined three-dimensional structures of peptides or proteins, referred to as protein folding (Gething and Sambrook, 1992, Nature 355:283-437) by the person skilled in the art, is crucial for the biological function of peptides or proteins. The defined folding of proteins (tertiary structure) is important for the production of biologically active molecules and it takes place after the amino acid units link to form the primary structure. There are also numerous biological functions which are based on a change of the three-dimensional structure of peptides or proteins, wherein often only subareas of the polypeptide chain are changed. Such changes have been described for various biochemical processes (Wie-Jia O. et al., 1995, J. Biol. Chem., 270:18051-18059) as for example in case of transport of proteins through membranes (Quilty J A. and Reithmeier R A F, 2000, Traffic 1:987-998). With respect to the pathobiochemical processes which occur when protein structures change, diseases like cystic fibrosis, juvenile pulmonary emphysema, Tay-Sachs disease, congenital sucrose isomaltase deficiency or familial hypercholesterolemia have to be mentioned, the scrapie prion protein ($PrP^{Sc}$) occurring in connection with spongiform encephalopathy has been examined particularly well. Here, the three-dimensional structure of the $PrP^{Sc}$ is extremely different from the structure of the prion protein ($PrP^{C}$) of healthy individuals, although the primary structures of $PrP^{Sc}$ and $PrP^{C}$ are the same (Prusiner, 1991, Science 252:1515-1522). Currently, the processes causing the incorrect folding of proteins are not always known. Thus, currently, it is completely unknown how the incorrectly folded $PrP^{Sc}$ is formed in vivo from $PrP^{C}$. In vitro also this process has not yet been understood.

In contrast thereto, for specific proteins, the formation of a native protein from its unfolded peptide chain has been well described by means of biotechnological processes. Thus it becomes evident that the folding of the inordinate/unfolded peptide chain to a native protein contains fast and slow steps. One of the most known slow folding steps is caused by the cis/trans isomerisation of the tertiary amide prolyl peptide bonds (R—CO—X—R' with R,R'=aminoacyl or peptidyl; X=cyclo(-NCH(CONHR')—$CH_2CH_2CH_2$—) (e.g. Eberhardt E S. et al., 1996, JACS 118:12261-12266), whose biological and chemical properties are very different from secondary amide peptide bonds (—RC(O)NHR').

As has been proved by numerous scientific analyses, the folding rate of this slow folding step in vitro as well as in vivo is increased (Fischer G, 1994, Angew. Chemie Intl. ed. Engl. 33: 1415-1436) by catalysis of this isomerisation by means of peptidyl prolyl cis/trans isomerases (nomenclature no. EC 5.2.1.8), as e.g. by means of FK506-binding proteins (FKBP's) (Dumont F J, 2000, Current Medicinal Chemistry 7:731-48), while representatives of this class of enzymes cannot significantly catalyse the cis/trans isomerisation of secondary amide peptide bonds in oligo- and polypeptides (Scholz et al., 1998, Biol. Chem. 379, 361-365).

As could be demonstrated recently, the folding of proline-free proteins also contains slow folding steps (Pappenberger G. et al., 2001, Nature Structural Biology 8:452-458). Apparently, the cause is the temporary formation of protein forms with secondary amide peptide bonds in an unnatural cis-conformation, which cannot fit into the biologically active three-dimensional structure of the native protein. As opposed to the cis/trans-isomerisation of prolyl-peptide bonds, the cis/trans isomerisation speed of secondary amide peptide bond, which form 10 of the 20 genetically encoded amino acids, is approximately 100 times faster.

It was surprisingly found that the cis/trans-isomerisation of peptides containing secondary amide peptide bonds can be specifically accelerated in aqueous media by means of catalytic amounts of substances (catalysts).

Thus, by adding a homogenate of *Escherichia coli* or of a protein isolated therefrom (DnaK) (Example 7) to the test assay, the rate of the cis/trans-isomerisation of a considerably larger amount e.g. of the alanyl tyrosine peptide bond in Ala-Ala-Tyr-Ala-Ala (SEQ ID No.1) or e.g. of the Ala-Leu peptide bond in alanyl leucine is accelerated (catalysed) specifically and in repeated cycles over a period of weeks without a loss in activity, without the peptide bond being destroyed as a side reaction or without the oligopeptide being chemically changed in another manner (Examples 1 and 8). It is also assumed that a corresponding endogenous enzymatic activity takes place in mammals.

Figure 1:
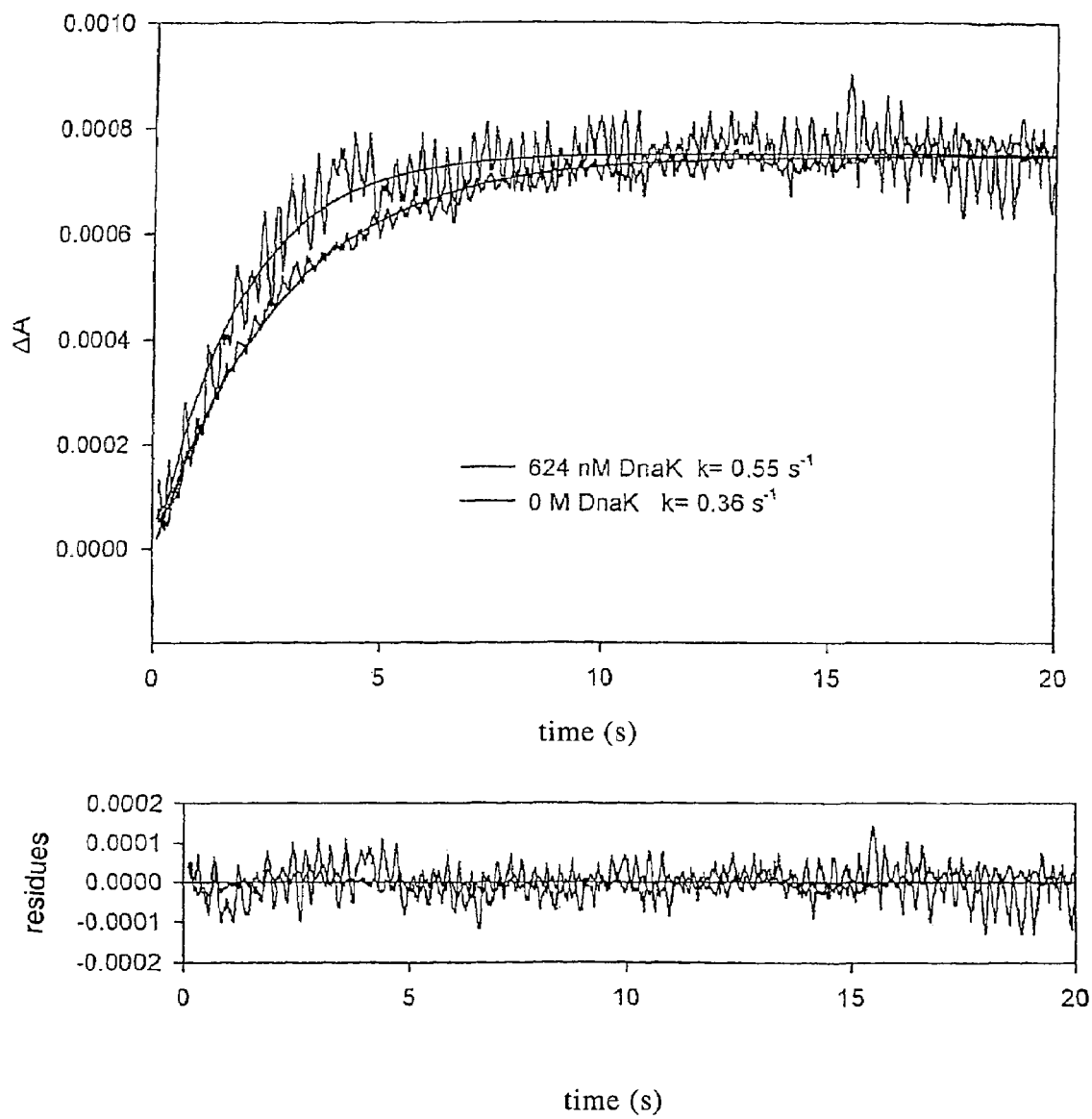
FIG. 1 is a graph of the cis/trans isomerisation of the peptide bond of the substrate Ala-Leu as shown by a spectroscopic change of the substrate in the range of 2220-228 nm over a period of time.

The subject matter of the surprisingly found catalysis are peptide bonds in oligopeptides and proteins of the Xaa-Yaa type, with Xaa including all natural amino and imino acids and Yaa including all natural amino acids but excluding imino acids. Secondary amide peptide bonds which are formed from chemically modified amino acids are also subject matter of the catalysis. Such amino acids are created by post translational modifications of oligopeptides and proteins in vivo (e.g. Williams KR. Stone KL., 1995, Methods in Molecular Biology 40:157-75). A catalysis of the cis/trans-isomerisation of secondary amide peptide bonds by the protein-based catalysts isolated from biological material (enzymes), hereinafter referred to as "secondary amide peptide bond cis/trans isomerases" (APIases), is observed if by adding a necessary but always catalytic amount of the enzyme under appropriate conditions an acceleration of the cis/trans isomerisation of the observed secondary amide peptide bond can be detected. An acceleration by APIases can be observed when the isomerisation rate is higher than the error-prone speed without APIase. Under optimum conditions, the necessary amount of the catalysts lies under 0.01% of the concentration of the molecule containing the peptide bond to be catalysed. However, it can also be necessary to choose a necessary amount of catalyst which is by far higher than the concentration of the molecule containing the peptide bond to be catalysed.

In this context, as is known to the person skilled in the art, the term "peptide" means condensation products of two or more amino acids with acid amide-like linkage, the term "oligopeptides" particularly refers to peptides with two to ten amino acid residues.

Preferably, catalysis of the invention is observed in buffer solutions, e.g. 0.1 m phosphate buffer, pH 7.4. However, the aqueous media used can also consist of systems with several phases, which e.g. formed by the combination of polymers with chaotropic reagents, as is described e.g. in U.S. Pat. No. 5,723,310. Hereby, the protein concentration of the aqueous solution, in which the catalysis of the invention takes place has to be at a level which does not essentially decrease the catalytic function of the catalyst, i.e. by not more than 98%. Embodiments of the invention can use the catalyst in dissolved form but also bound to solid surfaces, or also compartmentalized in microstructures, such as e.g. encapsulated.

Within the meaning of the invention, the specific catalysis of the cis/trans isomerisation of secondary amide peptide bonds is an essential property of these catalysts. The formation of a complex between the catalyst and the substrate within a limited period of time is understood as specific within the meaning of the invention, the biochemical constants of this complex such as formation and disintegration rate in the desired reaction direction can not only be influenced by the interaction of the catalysts with the peptide bond itself but also by the direct interaction of the catalyst with chemical functionalities adjacent to this peptide bond (so-called secondary binding-sites). The catalysis, too, of the cis/trans isomerisation of peptide bonds by protons or hydroxylic ions is unspecific as the essential feature of a specific catalysis, the suppression of side reactions (here e.g. the hydrolysis of secondary amide peptide bonds) and the acceleration of the desired reaction only is not given. Example 8 shows an example for a specific APIase catalysis. Apart from the unspecific catalysis of the cis/trans isomerisation of secondary amide peptide bonds by protons or hydroxylic ions, the relatively well-analyzed (abstract in C. Cox and T. Lecta, 2000 Accounts of Chemical Research 33:849-858) catalysis by metal ions (Lewis acids) can be cited. It can be differentiated from the catalysis of the invention by the specificity in aqueous solutions as the Lewis acids used induce side reactions (e.g. peptide bond hydrolysis: Grant KB, Patthabi S., 2001, Anal. Biochem. 289:196-201) or side chain oxidations (Huang XD et al., 1999, Biochem. 38:7609-16), Li SH. et al., 1995, Biotech&Bioengineering 48:490-500) or can even be used as reaction partner themselves (Zou J, Sugimoto N., 2000, Biometals 13:349-359; Casalaro et al., 2001, Polymer 42:903-912; Sun S. et al., 2000, Organic Letters 2:911-914) to form undesired products while consuming the starting materials.

The structure and conformation of the complex between APIase and a substrate which forms within a certain period of time can be used to predict inhibitors if the three-dimensional structure is provided. Thus, by means of the known three-dimensional peptide bond structure of the APIase DnaK (Wang H. et al., 1998, Biochemistry, 37:7929-7940, Zhu X. et al., 1996, Science 272:1606-1614) and empiric calculations which are known to the person skilled in the art (e.g. Kasper P. et al., 2000, Proteins 40:185-192) and studies with respect to bonds of DnaK to peptide libraries (Rüdiger S. et al., 1997, EMBO J. 16:1501-1507; Rüdiger S. et al., 2000, J. Mol. Biol. 304:245-251; Mayer M P. et al., 2000, Biol. Chem., 381:877-885) the binding pocket of the protein DnaK can be predicted as hydrophobic binding site for three amino acid residues which are flanked by negatively charged residues which can bind to basic amino acid residues.

The surprising finding that DnaK has APIase activity makes it possible to specify the data obtained from the structural data and the binding studies, while referring to APIase activity measurements and their inhibition, in such a way that they are also suitable for finding inhibitors of the APIase activity of DnaK, or also to exclude peptides as inhibitors. By finding the APIase activity, inhibitors of this activity can be found. The present invention provides substances which can inhibit the APIase activities of proteins. The inhibitors of this invention include all molecules which bind to the active center of APIases and as a consequence of the binding to the APIase inhibit its APIase activity.

The present discovery also includes APIase inhibitors which imitate the structure and conformation of the APIase substrate, when it is bound in the active centre of the APIase.

The inhibitors of the present discovery have a typical inhibition constant of 100 micro molar or less. Also included are organic molecules which imitate the structure and conformation of a peptide bond R2-R3 which bind to the APIases and thereby inhibit their APIase activity, when R2 represents all natural amino acids and R3 includes the following amino acids: methionine, alanine, serine, glutamic acid, leucine, lysine, isoleucine and glycine.

Inhibitors of the present discovery include compounds consisting of a core region (binding motif) which imitate the structure and conformation of a peptide bond R2-R3 which bind to APIases and thereby inhibit their APIase activity, if R2 represents all natural amino acids and R3 includes the following amino acids: methionine, alanine, serine, glutamic acid, leucine, lysine, isoleucine and glycine.

The inhibitors of the present invention comprise compounds whose binding motif is flanked on the one side by hydrophobic groups and on the other side of the binding motif by hydrophobic or positively charged groups, the flanking groups being in electrostatic or hydrophobic contact to the catalytic centre of the APIase in question.

The present invention particularly comprises peptides and polypeptides as inhibitors of APIase activity. The peptides and polypeptides of the present invention are naturally occurring amino acids (e.g. L-amino acids) and small molecules, which can simulate the inhibiting peptides as so-called peptide analogues, derivatives or mimetics biologically or biochemically (Saragovi H U., et al., 1992, 10:773-778).

The polypeptide or peptide inhibitors of the present invention can have a linear or a cyclic conformation. Compounds having an APIase-inhibiting activity can be determined by degenerated peptide libraries and the APIase activity assay described herein.

Inhibitors of the invention can have a length of from 2 to 200 amino acids. Preferably, however, these inhibitors consist of 2 to 20 amino acid residues and in a particular embodiment of 3 to 6 amino acid residues. APIase inhibitors of a particularly suitable embodiment consist of 4 amino acid residues with the following consensus sequence: $R^1$—$R^2$—(CONH)—$R^3$—$R^4$, in which R1, R2 and R4 can represent any natural L-amino acid and R3 exclusively represents L-amino acids methionine, alanine, serine, glutamic acid, leucine, lysine, Isoleucine and glycine.

The inhibitors of the invention can be synthesized by means of standard methods which are generally known and which include standard techniques of solid phase synthesis. The inhibitors consisting of natural amino acids can also be produced by recombinant DNA techniques. The inhibitors of this invention are either constructed of the 20 naturally occurring amino acids or other synthetic amino acids.

Synthetic amino acids include e.g. naphthylalanine, L-hydroxy-propyl-glycine, L-3,4-dihydroxy-phenylalanine and amino acids such as L-alpha-hydroxy-lysine and L-alpha-methyl-alanine but also beta amino acids such as e.g. beta-alanine and isoquinoline. Other suitable non-natural amino acids can be amino acids whose normal side chain of 20 natural amino acids has been replaced by other side chains, e.g. with such groups as long chain and short chain alkyl residues, cyclic 4-, 5-, 6- to 7-membered alkyl rings, amides, alkylated amides, alkylated diamides, short chain alkoxy groups, hydroxylic and carboxylic groups and short chain esters and their derivatives or 4-, 5-, 6- to 7-membered hetereocycles. The term short chain alkyl residue refers to linear and branched chains of alkyl groups with 1 to 6 carbon atoms such as methyl, ethyl, propyl, butyl etc. The term short term alkoxy groups describes linear and branched chains of alkoxy groups consisting of 1 to 16 carbon atoms, such as e.g. methoxy, ethoxy etc.

Cyclic groups can be saturated or unsaturated. The unsaturated can be aromatic or non-aromatic.

In this context, C5- to C34-carbocyclic structures comprise saturated and unsaturated mono and bicyclic compounds with 5 to 34 carbon atoms, particularly cyclopentane, cyclohexane, cycloheptane, cyclooctane, cyclononane, cyclodecane, cycloundecane, cyclododecane, cyclopentene, cyclohexene, cycloheptene, cyclooctene, cyclononene, cyclodecene, cycloundecene, cyclododecene, cyclopentane, cylcohexane, cycloheptane, cyclooctane, cyclononane, cylcodecane, cycloundecane, cyclododecane, cyclopentene, cyclohexene, cycloheptene, cyclooctene, cyclononene, cyclodecene, cycloundecene, cyclododecene, bicyclohexane, bicycloheptane, bicyclooctane, bicyclononane, bicyclodecane, bicycloundecane, bicyclododecane, bicycloheptene, bicyclooctene, bicyclononene, bicyclodecene, bicycloundecene, bicyclododecene, and C5-up to C34-spiro compounds and condensed ring systems such as e.g. decaline, hydrindane.

According to the invention, the following groups are referred to as benzoic or non-benzoic aromatic compounds: benzene, naphthalene, cyclopentadiene, indene, fluorine, indane and tetraline.

In this context, benzole and naphthalene are particularly preferred.

Moreover, R2 and R3 can represent saturated or unsaturated isocycles (a), such as (a1) monocyclic compounds with a ring size between 5 to 7 carbon atoms, such as (a2) molecules, having several but independent rings in the molecule and being either directly linked to each other such as biphenyl or being linked to each other by intermediate members such as diphenylmethane, or such as (a3) polycycles which are o-condensed such as indene (a31) or having more than two common C-atoms in the rings such as camphane (a32) or (a33) where, due to pericondensation, more than two C-atoms are members of several rings at the same time, as is the case with respect to acenaphthene, or (a34) which, such as spiranes, two rings each have a common quarternary C-atom, as is also the case of molecules (a4) having an aliphatic nature and are attributed either to the monoterpenes with the molecular formula $C_{10}H_{16-20}$ or to the bicyclic terpenes, the sesquiterpenes, the diterpenes or the triterpenes, wherein the basic body of the amino acid mimetic can also be aromatic (a5) and can either consist of a ring with 6 carbon atoms or, as is the case with pure aromatic compounds, from (a51) condensed ring systems, (a52) uncondensed cyclic ring systems or comprises (a53) other condensed ring systems.

In particular, heterocyclic groups have a ring size of 5 to 8 carbon atoms, typically contain one or more hetero atoms such as nitrogen, oxygen and/or sulphur, such as e.g. furazanyl, furyl, imidazolidinyl, imidazolyl, imidazolinyl, indolyl, isothiazolyl, isoxazolyl, morpholinyl (e.g. morpholino), oxazolyl, piperazinyl (e.g. 1-piperazinyl) piperidyl (e.g. 1-piperidyl, piperidino) pyranyl, pyrazinyl, pyrazolidinyl, pyrazolinyl, pyrazolyl, pyridazinyl, pyridyl, pyrimidinyl, pyrrolidinyl (e.g.: 1-pyrrolidinyl), pyrrolinyl, pyrrolyl, thiadiazolyl, thiazolyl, thienyl, thiomorpholinyl, (e.g. thiomorpholino) and triazolyl. The heterocyclic groups can be substituted or unsubstituted. When a group is substituted, the substituent can be alkyl, alkoxy, halogen, oxygen or a substituted or unsubstituted phenyl residue (U.S. Pat. Nos. 5,654, 276 and 5,643,873).

The term "amino acid mimetics" as used in the present invention for R2 and R3, refers to structures as described or produced in AU658636, CN1069735, AU1829792, EP0519640, CA2071061, U.S. Pat No. 5422426, ZA9204244, IE7585892. Moreover, instructions for their production can be found in the following documents:

Hruby V J. Slate C A. Amino acid mimetics and design of peptidomimetics for opioid and melanocortin receptors: General perspectives. [Article] ADVANCES IN AMINO ACID MIMETICS AND PEPTIDOMIMETICS, VOL 2, 1999. 2 PG. 191-220.1999., Scholz D. Weber-Roth S. Macoratti E. Francotte E. Expedient synthesis of alpha-substituted alpha, beta-unsaturated gamma-amino acids (dipeptide mimetics); Wittig reaction of alpha-amino aldehydes with alpha-substituted alkoxycarbonyl phosphoranes. [Article] Synthetic Communications. 29(7):1143-1155, 1999., AMINO ACIDS AND PEPTIDES—LII—DESIGN AND SYNTHESIS OF OPIOID MIMETICS CONTAINING A PYRAZINONE RING AND EXAMINATION OF THEIR OPIOID RECEPTOR BINDING ACTIVITY. [Article] Chemical & Pharmaceutical Bulletin. 46(9):1374-1382, 1998 September, Burger K. Mutze K, Hollweck W. Koksch B. INCORPORATION OF ALPHA-TRIFLUOROMETHYL SUBSTITUTED ALPHA-AMINO ACIDS INTO C- AND N-TERMINAL POSITION OF PEPTIDES AND PEPTIDE MIMETICS USING MULTICOMPONENT REACTIONS. [Article] Tetrahedron. 54(22):5915-5928, 1998 May 28., Hanessian S. Mcnaughtonsmith G. Lombart H G. Lubell W D. DESIGN AND SYNTHESIS OF CONFORMATINALLY CONSTRAINED AMINO ACIDS AS VERSATILE SCAFFOLDS AND PEPTIDE MIMETICS [Review]. [Review] Tetrahedron. 53(38): 12789-12854, 1997 Sep. 22., Sabol J S. Flynn G A. Friedrich D. Huber E W. CONSTRAINED AMINO ACIDS—THE SYNTHESIS OF GLUTAMINE MIMETICS. [Article] Tetrahedon Letters. 38(21):3687-3690, 1997 May 26., Moree W J. Sears P. Kawashiro K. Witte K. Wong C H. EXPLOITATION OF SUBTILISIN BPN' AS CATALYST FOR THE SYNTHESIS OF PEPTIDES CONTAINING NONCODED AMINO ACIDS, PEPTIDE MIMETICS AND PEPTIDE CONJUGATES. [Article] Journal of the American Chemical Society. 119(17):3942-3947, 1997 Apr. 30., Lombart H G. Lubell W D. RIGID DIPEPTIDE MIMETICS—EFFICIENT SYNTHESIS OF ENANTIOPURE INDOLIZIDINONE AMINO ACIDS. [Article] Journal of Organic Chemistry. 61(26):9437-9446, 1996 Dec. 27., Reetz M T. Griebenow N. Goddard R. STEREOSELECTIVE SYNTHESES OF ALPHA-HYDROXY-GAMMA-AMINO ACIDS—POSSIBLE GAMMA-TURN MIMETICS. [Article] Journal of the Chemical Society—Series Chemical Communications. (16):1605-1606, 1995 Aug. 21., Liao, Subo. DESIGN AND SYNTHESIS OF TOPOGRAPHICALLY CONSTRAINED AMINO ACIDS, AND BIOACTIVE PEPTIDES FOR STUDIES OF LIGAND-RECEPTOR INTERACTION, AND FOR DE NOVO DESIGN OF DELTA-OPIOID SELECTIVE NON-PEPTIDE MIMETICS AS POTENTIAL THERAPEUTICS. Dissertation Abstracts International. Volume: 58-08, Section: B, page: 4232., Borg, Susanna. HETEROCYCLIC PEPTIDE MIMETICS DERIVED FROM BOC-AMINO ACIDS: DESIGN, SYNTHESIS AND INCORPORATION IN SUBSTANCE P AND DERMORPHIN. Dissertation Abstracts International. Volume: 57-02, Section: C, page: 0591., Nesloney, Carey Lynn. BIPHENYL-BASED UNNATURAL AMINO ACIDS DESIGNED TO NUCLEATE BETA-SHEET STRUCTURE AND PROGRESS TOWARDS TRIPHENYL-BASED NON-PEPTIDE ALPHA-HELIX MIMETICS. Dissertation Abstracts International. Volume: 56-10, Section:B, page: 5498., Markwell R E. Rahman SS. Ward R W. Synthesis of aminoazalactams as cyclic mimetics of basic alkyl amino acids. [Journal] BIOORG MED CHEM LETT, Vol 3(12) (pp 2537-2540), 1993., Rico J G. Synthesis of novel beta-amino acid precursors: beta-Amino-hydrocoumarins as unusual aspartic acid mimetics used in fibrinogen receptor.

Reference is made to the complete content of the documents cited above.

The term "peptide mimetics" as used in the present invention for R2 and R3, structures as described in Okada Y. Fukumizu A. Takahashi M. Yamazaki J. Yokoi T. Tsuda Y. Bryant S D. Lazarus L H. Amino acids and peptides. LVI. Synthesis of pyrazinone ring-containing opioid mimetics and examination of their opioid receptor binding activity. [Journal] Tetrahedron. Vol 55(50) (pp 14391-14406), 1999.

Andrade-Gordon P. Maryanoff B E. Derian C K. Zhand H-C. Addo M F. Darrow A L. Eckardt A J. Hoekstra W J. McComsey D F. Oksenberg D. Reynolds E E. Santulli R J. Scarborough R M. Smith C E. White K B. Design, synthesis, and biological characterisation of a peptide-mimetic antagonist for a tethered-ligand receptor. [Journal] Proceedings of the National Academy of Sciences of the United States of America. Vol 96(22) (pp 12257-12262), 1999.

Ikada Y. Fukumizu A. Takahashi M. Yamazaki J. Yokoi T. Tsuda Y. Bryant S D. Lazarus L H. Amino acids and peptides. LVI Synthesis of pyrazinone ring-containing opioid mimetics and examination of their opioid receptor binding activity. [Journal] Tetrahedron. Vol 55(50) (pp 14391-14406), 1999.

Andrade-Gordon P. Maryanoff B E. Derian C K. Zhang H-C. Addo M F. Darrow A L. Eckardt A J. Hoekstra W J. McComsey D F. Oksenberg D. Reynolds E E. Santulli R J. Scarborough R M. Smith C E. White K B. Design, synthesis, and biological characterization of a peptide-mimetic antagonist for a tethered-ligand receptor. [Journal] Proceedings of the National Academy of Sciences of the United States of America. Vol 96(22) (pp 12257-12262), 1999.

Li M. Lin Z. Johnson M E. Structure-based design and synthesis of novel thrombin inhibitors based on phosphinic peptide mimetics. [Journal] Bioorganic & Medicinal Chemistry Letters. Vol 9(14) (pp 1957-1962), 1999.

Boatman P D. Ogbu C O. Eguchi M. Kim H-O. Nakanishi H. Cao B. Shea J P. Kahn M. Secondary structure peptide mimetics: Design, synthesis, and evaluation of beta-strand mimetic thrombin inhibitors. [Journal] Journal of Medicinal Chemistry. Vol 42(8) (pp 1367-1375), 1999.

Deghenghi R. Synthetic peptides and their non-peptidyl mimetics in endocrinology: From synthesis to clinical perspectives. [Journal] Journal of Endocrinological Investigation. Vol 21(11) (pp 787-793), 1998.

Yang H. Sheng X C. Harrington E M. Ackermann K. Garcia A M. Lewis M D. Synthesis of sulfur-containing olefinic peptide mimetic farnesyl transferase inhibitors using the Nozaki-Hiyama-Kishi reaction and cuprate S(N)2' displacements. [Journal] Journal of Organic Chemistry. Vol 64(1) (pp 242-251), 1999.

Okada Y. Tsukatani M. Taguchi H. Yokoi T. Bryant S D. Lazarus L H. Amino acids and peptides. LII. Design and synthesis of opioid mimetics containing a pyrazinone ring and examination of their opioid receptor binding activity. [Journal] Chemical & Pharmaceutical Bulletin. Vol 46(9) (pp 1374-1382), 1998.

Kent D R. Cody W L. Doherty A M. The asymmetric synthesis of arginine mimetics: Derivatives of (S)-2-, 3- and 4-amidinophenylalanine suitable for incorporation into enzyme inhibitors and/or peptides. [Journal] Journal of Peptide Research. Vol 52(3) (pp 201-207), 1998.

Bisang C. Jiang L. Freund E. Emery F. Bauch C. Matile H. Pluschke G. Robinson J A. Synthesis, conformational properties, and immunogenicity of a cyclic template-bound peptide mimetic containing an NPNA motif from the circumsporozoite protein of *plasmodium falciparum*. [Journal] Journal of the American Chemical Society. Vol 120(30) (pp 7439-7449), 1998.

Burke T R Jr. Yao Z-J. Zhao H. Milne G W A. Wu L. Zhang Z-Y. Voigt J H. Enantioselective synthesis of nonphosphorus-containing phosphotyrosyl mimetics and their use in the preparation of tyrosine phosphatase inhibitory peptides. [Journal] Tetrahedon. Vol 54(34) (pp 9981-9994), 1998.

Tselios T. Probert L. Kollias G. Matsoukas E. Roumelioti P. Alexopoulos K. Moore G J. Matsoukas J. Design and synthesis of small semi-mimetic peptides with immunomodulatory activity based on myelin basic protein (MBP). [Journal] Amino Acids. Vol 14(4) (pp 333-341), 1998.

Hanessian S. McNaughton-Smith G. Lombart H-G. Lubell W D. Design and synthesis of conformationally constrained amino acids as versatile scaffolds and peptide mimetics. Tetrahedron report number 426. [Journal] Tetrahedron. Vol 53(38) (pp 12789-12854), 1997.

Pfeifer M E. Linden A. Robinson J A. 111. Synthesis of a novel tricyclic dipeptide template and its incorporation into a cyclic peptide mimetic containing an NPNA motif. [Journal] Helvetica Chimica Acta. Vol 80(5) (pp 1513-1527), 1997.

Wipf P. Henninger T C. Solid-phase synthesis of peptide mimetics with (E)-alkene amide bond replacements derived from alkenylaziridines. [Journal] Journal of Organic Chemistry. Vol 62(6) (pp 1586-1587), 1997.

Lenman M M. Ingham S L. Gani D. Synthesis and structure of cis-peptidyl prolinamide mimetics based upon 1,2,5-triazepine-3,6-diones. [Journal] Chemical Communications. Vol 1(1) (pp 85-87), 1996.

Qian Y. Vogt A. Sebti S M. Hamilton A D. Design and synthesis of non-peptide Ras CAAX mimetics as potent farnesyltransferase inhibitors. [Journal] Journal of Medicinal Chemistry. Vol 39(1) (pp 217-223), 1996.

Gramberg D. Weber C. Beeli R. Inglis J. Burns C. Robinson J A. Synthesis of a type-VIbeta-turn peptide mimetic and its incorporation into a high-affinity somatostatin receptor ligand. [Journal] Helvetica Chimica Acta. Vol 78(6) (pp 1588-1606), 1995.

Olson G L. Cheung H-C. Chiang E. Madison V S. Sepinwall J. Vincent G P. Winokur A. Gary K A. Peptide mimetics of thyrotropin-releasing hormone based on a cyclohexane framework: Design, synthesis, and cognition-enhancing properties. [Journal] Journal of Medicinal Chemistry. Vol 38(15) (pp 2866-2879), 1995.

Gomez Monterrey I M. Gonzalez-Muniz R. Herranz R. Garcia-Lopez M T. Synthesis of 8-amino-3-oxoindolizidine-1-carboxylic acid derivatives as conformationally restricted templates for use in design of peptide mimetics. [Journal] Tetrahedron. Vol 51(9) (pp 2729-2736), 1995.

Dodd D S. Kozikowski A P. Cusack B. Richelson E. Synthesis of partially non-peptidic neurotensin mimetics. [Journal] BIOORG MED CHEM LETT, Vol 4(10) (pp 1241-1246), 1994.

Ripka W C. De Lucca G V. Bach A C II. Pottorf R S. Blaney J M. Protein Beta-turn mimetics II: Design, synthesis, and evaluation in the cyclic peptide gramicidin S. [Journal] Tetrahedron. Vol 49(17) (pp 3609-3628), 1993.

Ripka W C. De Lucca G V. Bach A C II. Pottorf R S. Blaney J M. Protein beta-turn mimetics. I. Design, synthesis, and evaluation in model cyclic peptides. [Journal] Tetrahedron. Vol 49(17) (pp 3593-3608), 1993.

Nagai U. Sato K. Nakamura R. Kato R. Bicyclic turned dipeptide (BTD) as a beta-turn mimetic; its design, synthesis and incorporation into bioactive peptides. [Journal] Tetrahedron. Vol 49(17) (pp 3577-3592), 1993.

Currie B L. Krstenansky J L. Lin Z-L. Ungwitayatorn J. Lee Y-H. Del Rosario-Chow M. Sheu W.-S. Johnson M E. Design and synthesis of a bicyclic non-peptide beta-bend mimetic of enkephalin. [Journal] Tetrahedron. Vol 49(17) (pp 3489-3500), 1993.

Singh J. Gordon T D. Earley W G. Morgan B A. An efficient synthesis and acylation of alpha-amino-beta-keto-esters: Versatile intermediates in the synthesis of peptide mimetics. [Journal] Tetrahedron Letters. Vol 34(2) (pp 211-214), 1993.

Sato M. Lee J Y H. Nakanishi H. Johnson M E. Chrusciel R A. Kahn M Design, synthesis and conformational analysis of gamma-turn peptide mimetics of bradykinin. [Journal] Biochemical & Biophysical Research Communications. Vol 187(2) (pp 999-1006), 1992.

Krstenansky J L. Del Rosario-Chow M. Currie B L. The synthesis of syn- and anti-2(S)-phthalimidomethyl-2,3,4, $4^a,7,7^a$-hexahydro-6-oxo-5H-pyrano-[2,3-b]pyrroles as rigid beta-bend peptide-mimetics. [Journal] Journal of Heterocyclic Chemistry. Vol 29(4) (pp 707-711), 1992.

Gonzalez-Muniz R. Dominguez M J. Garcia-Lopez T. Cativiela C. Garcia J I. Mayoral J A. Synthesis of 2-substituted 8-amino-3-oxoindolizidine-2-carboxylic acid derivatives as peptide conformation mimetics. [Journal] Tetrahedron. Vol 48(24) (pp 5191-5198), 1992.

Kahn M. Chen B. Methodology for the synthesis of mimetics of peptide beta-turns. [Journal] Tetrahedron Letters. Vol 28(15) (pp 1623-1626), 1987.

Kullmann W. Design, synthesis, and binding characteristics of an opiate receptor mimetic peptide. [Journal] Journal of Medicinal Chemistry. Vol 27(2) (pp 106-115), 1984.

Reference is made to the complete content of the documents cited above.

Biologically active derivatives or analogues of the inhibitors described above, hereinafter described as peptide mimetics, can be produced according to the state of the art by the person skilled in the art (U.S. Pat. Nos. 4,612,132, 5,643,873, 5,654,276). These mimetics are based on a specific APIase inhibitor sequence while maintaining corresponding positions with respect to the basic inhibitors. These peptide mimetics have a biological activity (i.e. APIase inhibiting activity) which is comparable to the biological activity of the basic inhibitor. The peptide mimetic, however, have a "biological advantage" over the basic peptide inhibitor with respect to one or more of the following properties: solubility, stability and insensitivity as to hydrolysis and proteolysis.

Methods to produce such peptide mimetics include the modification of the N-terminal amino group, the C-terminal carboxy group and the modification of one or more peptide bonds of the peptide to non-peptidic bonds. In this context, it can be advantageous to carry out two or more of such modifications for the production of such peptide mimetics. In the following, examples of modifications of peptides are given which lead to the production of peptide mimetics. The corresponding techniques are described e.g. in U.S. Pat. Nos. 5,643,873 and 5,654,276. These techniques are used to produce mimetics of APIase inhibitors.

Modifications of the N-terminus: After solid phase synthesis of the peptide inhibitor the N-terminal protective group is selectively removed in such a way that all other functional groups remain protected and the molecule remains linked to the solid phase by means of the C-terminus. In this way it is possible to modify the N-terminus of the peptide in such a way that it corresponds to the desired mimetic.

Modifications of the N-terminus include: alkylation, acetylation, addition of a carbobenzoyl group, formation of a succinimide residue etc. In detail, the N-terminal amino group can be reacted as shown in the following:

a) With an acid halide (e.g. RC(O)Cl) or acid anhydride to form an amide group of the formula RC(O)NH—wherein R corresponds to the definition given above. The reaction is typically carried out with equimolar amounts or an excess (e.g. approximately 5 equivalents) of an acid halide compared to the peptide in an inert solution (e.g. dichloromethane), to which preferentially an excess (e.g. approx. 10 equivalents) of a tertiary amine such as e.g. diisopropylethylamine is added in order to capture the acid formed during the reaction. Conventional reaction conditions, e.g. room temperature for 30 minutes, are generally sufficient. The reaction indicated is also suitable to produce N-alkylamides of the general formular RC(O)NR.

b) With succinic acid to form a succinimide group. As indicated above, either equimolar amounts or an excess of the anhydride (e.g. approx. 5 equivalents) are necessary in order to convert the N-terminal amino group into a succinimide group. The methodology used and the use of an excess (e.g. 10 equivalents) of a tertiary amine such as e.g. diisopropylethylamine in a common inert solvent (e.g. dichloromethane) are generally known and is described e.g. in the U.S. Pat. No. 4,612,132, including numerous references to literature. The succinimide group itself can be substituted as e.g. by $C_2$-$C_6$ alkyl residues or—SR substituents which can be produced by methods known to the person skilled in the art. Such alkyl substituents can be produced e.g. as described in U.S. Pat. No. 4,612,132 by a maleic acid anhydride method and in the same way the corresponding—SR compounds by a reaction of RSH with maleic acid anhydride, wherein R remains as defined above.

c) To form a benzyloxycarbonyl-NH or a substituted benzyloxycarbonyl-NH-group by reaction with e.g. an equivalent or an excess of CBZ-Cl (i.e. benzyloxycarbonylchloride) or a substituted CBZ-Cl in a common inert solvent (such as e.g. dichloromethane) which preferably contains a tertiary amine to capture the acid which forms during the reaction.

d) To form a sulfonamide group by reaction with an equivalent amount or an excess (e.g. 5 equivalents) of R—S(O)$_2$CL in a common inert solvent (such as e.g. dichloromethane). Preferably, the inert solvent contains an excess of tertiary amine (e.g. 10 equivalents) such as e.g. diisopropylethylamine in order to catch the acid formed during the reaction. The reaction conditions are standard conditions known to the person skilled in the art, such as e.g. room temperature and a reaction time of approx. 30 minutes.

e) To form a carbamate group by reaction with an equivalent amount or an excess (e.g. 5 equivalents) of R—OC(O)CL or R—OC(O)$C_6H_4$-p-NO$_2$ in a common inert solvent (such as e.g. dichloromethane). Preferably, the inert solvent contains an excess of tertiary amine (e.g. approx. 10 equivalents) such as e.g. diisopropylethylamine in order to catch the acid formed during the reaction. The reaction conditions are standard conditions known to the person skilled in the art, such as e.g. room temperature and a reaction time of approx. 30 minutes; and f) To form a urea moiety of the general formula RNHC(O)NH— by reaction of the terminal amino group with an equivalent amount or an excess (e.g. 5 equivalents) of R—N=C=O in a common inert solvent (such as e.g. dichloromethane), wherein R was defined above. Preferably, the inert solvent contains an excess of tertiary amine (e.g. approx. 10 equivalents) such e.g. diisopropylethymanine in order to catch the acid built during the reaction. The reaction conditions are standard conditions known to the person skilled in the art, such as e.g. room temperature and a reaction time of approx. 30 minutes.

Modification of the C-terminus: For the production of peptide mimetics in which the C-terminal carboxyl group is replaced by an ester (e.g. —C(O)OR; R was defined above) corresponding synthetic resins are used which are known to the person skilled in the art. The compound having protective groups can be separated from the resin under basic conditions and alcohol (e.g. methanol). The desired ester can then be released from its protective groups (e.g. by adding HF) in the usual manner in order to obtain the desired ester.

In order to produce a peptide mimetic whose C-terminal moiety was replaced by the amide —C(O)NR$^3$R$^4$, a benzhydryl amino resin is used as carrier material for the peptide synthesis. After the termination of the synthesis, the addition of HF leads directly to the liberation of the free peptide amide (e.g. the C-terminus becomes —C(O)NH$_2$). Alternatively, if chloromethylated resins are used to obtain the free peptide amide, the synthesis product is cleaved from the resin by ammonia. If the cleavage is carried out with alkylamine or dialkylamine, the side-chain protected alkylamide or dialkylamide (i.e. the C-terminus is —C(O)NR$^1$R$^2$, wherein R$^1$ and R$^2$ were defined above) can be obtained. The protection of the side chain can then, in turn, be removed as described above by adding HF in order to obtain the desired free amides, alkylamides or dialkylamides.

Alternatively, by removing the hydroxyl- (—OH) or the ester- (—OR) group, the C-terminal carboxyl group or the C-terminal ester can react with the N-terminal amino group to obtain a cyclic peptide. After e.g. successfully synthesizing and obtaining the free acid of the desired peptide, its free acid can be converted into an activated ester with a suitable carboxyl group activator, such as e.g. dicyclohexylcarbodiimide (DCC) by using corresponding solvents such as e.g. in mixtures with methylene chloride (CH$_2$Cl$_2$), or dimethylformamide (DMF). Diluted solutions of the peptide can be used for suppressing polymerisation products during the spontaneous cyclization. The method described is known to the person skilled in the art as a standard method.

Introduction of non-peptidic bonds: Peptide mimetics in which one or more of the peptide bonds [—C(O)NH—] have been replaced by such bonds as —CH$_2$— carbamate bond, phosphonate bond, —CH$_2$-sulfonamide bond, urea bond, secondary amine (—C$_2$NH—) bond, or an alkylated peptidyl bond [—C(O)NR$^6$— wherein R$^6$ corresponds to a lower alkyl residue] can be obtained by conventional synthesis by simply exchanging the amino acid to be replaced by the suitable protected amino acid analogue at the corresponding stage of the synthesis.

Suitable compounds are e.g. amino acid analogues in which the carboxyl group of the amino acid was replaced with a functional group which is suitable to form one of the bonds described above. For example: If the peptide bond —C(O)NR— in a peptide is to be replaced by a —CH$_2$-carbamate bond (—CH$_2$OC(O)NR—), the carboxyl group (—COOH) of a correspondingly protected amino acid is first reduced to an CH$_2$OH group and converted, with conventional methods, into a —OC(O)Cl or a para-nitrocarbonate —OC(O)O—

$C_6H_4$-p-$NO_2$ functionality. The reaction of such a functional group with the free amine or an N-terminus alkylated amine of a partially synthesized peptide at the solid phase leads to the formation of a $CH_2OC(/O)NR$ bond in the synthesised peptide.

The bonds mentioned above can be introduced in the compound to be synthesized in a similar manner according to the state of the art. A peptide bond can, e.g., be replaced by a $CH_2$-sulfonamide bond in the following manner: after reduction of the carboxyl group (—COOH) of a suitable, protected amino acid to a —$CH_2OH$ group, the hydroxyl group is used to introduce a tosyl residue by e.g. a reaction with toluene-4-sulfonylchloride according to standard methods. The reaction of the tosylated compound with e.g. thioacetic acid and subsequent hydrolysis and sulfochlorination leads to the —$CH_2$—$S(O)_2Cl$ residue which replaces the carboxyl group. The use of the amino acid analogue produced in this way in the peptide synthesis leads to the production of a peptide mimetic where a peptide bond was replaced by a —$CH_2S(O)2NR$-bond.

According to the state of the art, —$CH_2NH$-bonds can be introduced into the compound to be synthesized in a similar way to replace a peptide bond by means of a suitable dipeptide analogue wherein the carbonyl group of the peptide bond has been transformed to a $CH_2$ group by means of conventional methods. With respect to diglycine, e.g. the reduction of the amide provides the corresponding amine $H_2NCH_2CH_2NHCH_2COOH$ which can be used as an N-protected derivative for the next synthesizing step of the peptide synthesis of peptide mimetics.

The substitution of amino acids by such amino acid analogues during the synthesis of peptide mimetics can be carried out during any such synthesizing step, so that it is also possible to obtain mimetics in which all or only some of the peptide bonds have been replaced by non-peptidic bonds.

The inhibitors of the present discovery can also be cyclic peptides and cyclic peptide mimetics. Such cyclic inhibitors can be produced according to generally known techniques which have been described e.g. in U.S. Pat. No. 5,654,276 or U.S. Ser. No. 08/864,392 (28 May 1997).

In this context, peptides or peptide mimetics of the general basic structure

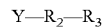

are preferred, wherein Y is a saturated or unsaturated, linear or branched-chain fatty acid which is linked to the amino acid or the amino acid mimetic $R_2$ by a C(O)NH bond, and wherein the amino acid or the amino acid mimetic $R_3$, via its amino group, is linked to $R_2$ by a C(O)NH bond.

In this context, particularly preferred compounds according to the invention are compounds of the following formulae:

37/B10

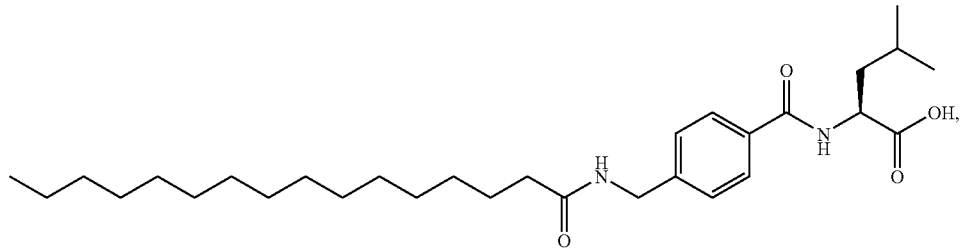

37/B11

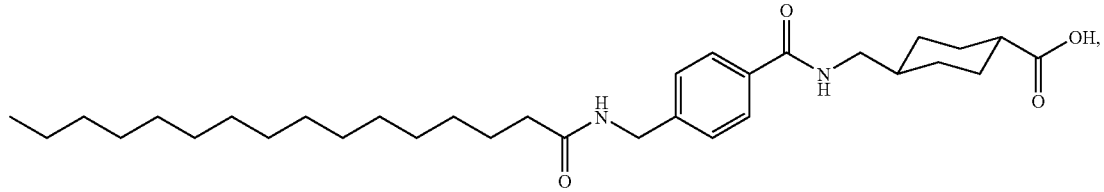

30/B04

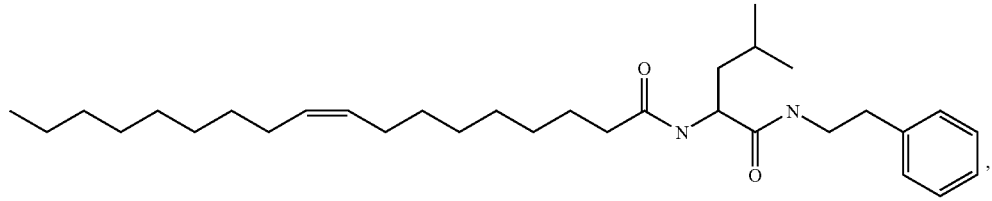

28/C8
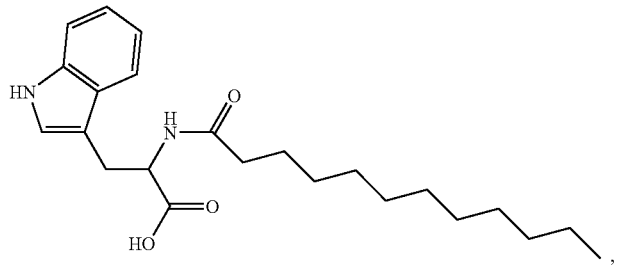
53/C3; N-lauroyl-rac.-phenylalanin
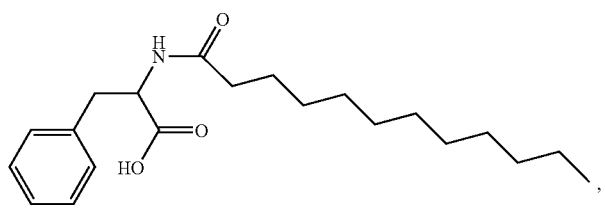
53/B5; echinocandin B
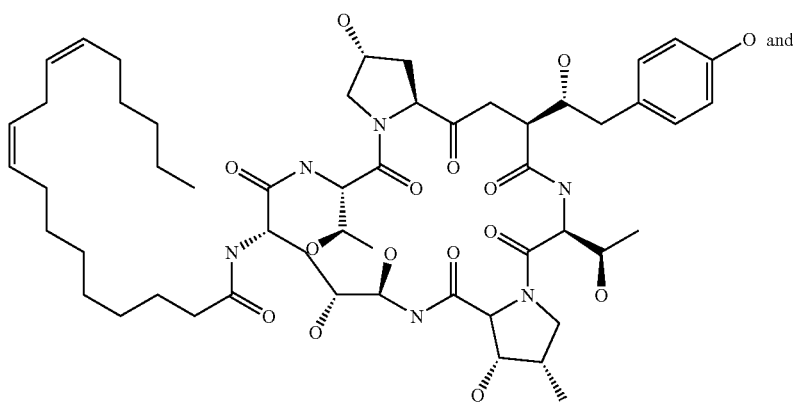
28/B7; N-lauroyl-L-asparagine acid
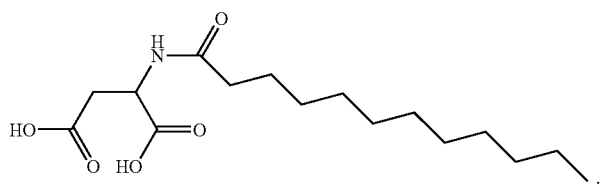
In this context, particularly preferred is
37/B10
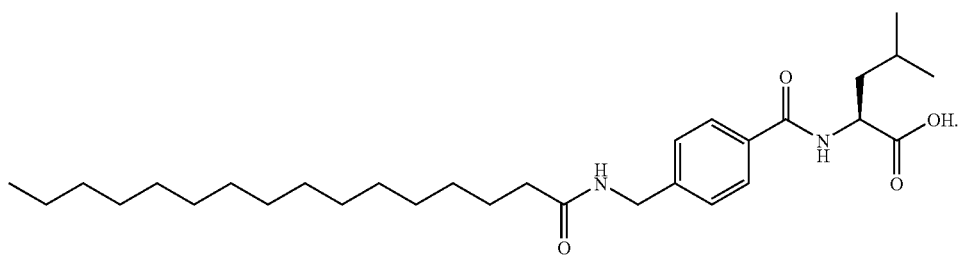

The biological activity of inhibitors according to the present discovery can, as stated above, be detected by means of its effect onto the APIase activity in corresponding APIase activity assays. Typically, inhibitors have an inhibition constant ($K_i$) which is in the nanomolar range or below, but at least lower than 100 micromolar, and even more preferred lower than 10 micromolar. Inhibition constants can be determined by methods generally known. For example, the $IC_{50}$ value denotes the molar concentration of an inhibitor as inhibition constant, which is necessary to reduce the activity of an enzyme measured under standard conditions by 50%.

Inhibitors according to the invention can also be used for influencing the division of cells. Thus, e.g. the growth of cells can be influenced by these inhibitors. Inhibitors of the APIase activity according to invention can be suitable to kill target cells. They can also be used as active agents for the treatment of infections by fungi or yeasts, including *Aspergillus*, and parasites (e.g. malaria) in mammals. The term mammals is to relate to domestic pets and humans, too.

Inhibitors according to the invention can also be used for influencing the division of cells. Thus, e.g. the growth of cells can be influenced by these inhibitors. Inhibitors of the APIase activity according to invention can be suitable to kill target cells. They can also be used to be employed as active agents for the treatment of infections by fungi or yeasts, including *Aspergillus*, and parasites (e.g. malaria) in mammals. The term mammals is to relate to domestic pets and humans, too.

For example, the APIase activity of DnaK is important for the correct folding of proteins. The correct folding, itself, is one of the preconditions for the most varied biochemical processes in the cell, such as e.g. mitosis or apoptosis. Therefore, the inhibition e.g. of DnaK with an inhibitor of its APIase activity according to the invention leads to the mitotic arrest of the cell and, subsequently, to apoptosis. In this way, APIase inhibitors can be used as therapeutically active agents for influencing neoplastic and hyperplastic diseases.

In this context, neoplastic and hyperplastic diseases include any forms of hyperproliferations, psoriasis, retinosis, atherosclerosis caused by plaque formation, leukaemias and benign ulcers. Also diseases such as lymphomas, papilomae, lung fibrosis, rheumatoid arthritis and multiple sclerosis.

The inhibition of the APIase activity can be a particular advantage in disease processes that lead to pathogenic changes by the formation of wrongly folded proteins. Apart from the diseases described above, such changes are also observed with diseases that occur with massive pathobiochemical changes in structure of proteins, such diseases including e.g. cystic fibrosis, juvenile pulmonary emphysema, Tay-Sachs syndromes, congenital sucrose isomaltose deficiency or familiar hypercholesterolaemia or transmissible spongiform encephalopathy (prion diseases). The administration of APIase inhibitors can influence these diseases in such a way that it can lead to the slowing down up to the remission of the course of disease. In this context, the present invention particularly relates to pharmaceutical compositions used for the treatment or prevention of the above diseases.

APIase inhibitors can also effectively have a positive influence on the course of bacterial infections, since it is known that APIases such as DnaK are necessary for the protein biosynthesis of the bacteria (Deuerling E. et al., 1999, Nature 400:693-6; Teter S A. et al., 1999, Cell. 97:755-65).

Inhibitors according to the invention can be used in mixtures in which the inhibitor represents the active compound. Suitable mixtures, often referred to as pharmaceutical mixture, may also contain a pharmaceutically acceptable carrier. The pharmaceutical mixture containing such inhibitor according to the invention can be used intravenously, parenterally, orally, by inhalation, by means of medicinal plasters or in form of suppositories such as e.g. suppositories to be administered rectally in medicine. The pharmaceutical mixture is administered either as a single dose or, however, in several doses over a period of time sufficient to accomplish a concentration of the active agent having the desired therapeutic effect.

Acceptable pharmaceutical carriers include substances such as e.g. water, saline solutions, alcohols, polyethylenglycol, gelatine, carbohydrates such as lactose, amylose or starch, magnesium stearates, talcum, paraffin oil, fatty acid esters, hydroxymethylcellulose, polyvinylpyrolidone, etc., but are not limited thereto. It may be necessary to sterilise the pharmaceutical mixture and to mix it with further additives of that kind, such as e.g lubricants, preservatives, stabilisers, wetting agents, emulsifying agents, salts to influence the osmotic pressure, buffers, colouring agents and/or aroma additives which do not or only marginally influence the active biological compound. It can also be an advantage to add further active agents to the pharmaceutical mixture, such as e.g. inhibitors of proteolytic enzymes, in order to delay or prevent the degradation of the inhibitor according to the invention.

In the case of parenteral administration it can be an advantage to use the injectable, sterile solution as oily or aqueous solution or as suspension or emulsion. The amount of the inhibitor used for a particular therapeutic application can also be influenced by the way of administration, the nature of the composition (formulation of the active agent), but also by the patient's individual properties such as e.g. the age, body weight or general condition. Therefore, an effective amount of the inhibitor is an amount sufficient to inhibit the desired APIase activity in such a way that the desired biological effects such as e.g. the purposeful influence of the cell growth of specific cells is triggered. Effective doses for a specific individual are determined according to common practice after general considerations (e.g. by means of a common pharmacological protocol).

The provision of a method allowing the detection of the catalysis of the cis/trans isomerisation of secondary amide peptide bonds by specific catalysts, the APIases and their low-molecular mimetics is a further subject matter of the invention. Due to the surprising finding that the cis/trans isomerisation of secondary amide peptide bonds by APIases can be specifically accelerated, there is the possibility of using methods for the assessment of the isomerisation rate to verify the specific catalysis by catalysts. The used methods that can be used according to the invention include direct methods for the detection of the isomerisation such as e.g. NMR methods (Example 8) or spectroscopic detection methods (Example 1-4, 6-7), but also indirect methods that use downstream biochemical reactions such as e.g. protein folding, hydrolysis or isomer-specific chemical reactions (such as e.g. phosphate transfer reactions). Due to biochemical reactions that take place downstream or in competition with the cis/trans isomerisation of a critical secondary amide peptide bond of the substrate, there can be measurable differences in the formation rate of the final or intermediate products of these reactions. Such quantifiable physical, chemical, biochemical or biological differences can be e.g. electrophoretic migratory rates, the formation of a fluorescence or UV/V is absorption signal, the recognition by means of antibodies or the transport across biological membranes.

The above method makes it possible for new catalysts with APIase activity in biological materials to be found. Due to isolation experiments of APIases from biological materials, there are indications to further existing catalysts, since the elution pattern is typical for a mixture of more than one catalytically active species.

There are further advantages by using the catalysed cis/trans isomerisation of secondary amide peptide bonds in polypeptides by APIases in the biochemistry/biotechnology. The biochemical/biotechnological preparation of proteins and other polypeptides is an essential feature of these areas (Yon J M., 2001, J. Med. & Biolog. Res. 34:419-435). Great difficulties in the economical production are often due to the process called protein folding. This process implies significant changes of the angles omega, phi and psi of the peptide chain backbone. If protein folding takes place, the folding leads to at least one new qualitative characteristic of the molecule exhibiting at least one of the peptide bonds changed in their three-dimensional structure. This new quality can be, e.g. in enzymes, the formation of a functional structure that the person skilled in the art calls "active centre" or a particular substrate specificity (Shinde U. et al., 1999, J. Biol. Chem. 274:15615-15621), the new quality can, however, also be a difference that can be detected only with difficulty by means of chemical, biochemical, biological or physical methods. Thus, charges of proteins that are produced in a biotechnological manner whose functional properties can be measured, such as e.g. enzymes, receptor proteins, inhibitors or hormones, which often show no differences in a great number of methods known to the person skilled in the art such as chromatography, mass spectrometry, amino acid analysis or circular dichroism, be differentiated by means of these functional properties (such as specific activity or titer concentration). Apart from the above, there is a series of examples wherein the structural differences are so great that they can be detected by relatively rough methods, such as e.g. differences in solubility. For example, a process during folding of proteins in the cell, the so-called aggregation, leads to the formation of inclusion bodies that can be dissolved in aqueous solutions with difficulty only (Kopito R R., 2000 Trends in Cell Biology 10:524-530).

The structural differences of the three-dimensional structure of peptide chains can, however, also mean that one quality, in comparison with the other, mostly consists of populations of random structures (random coil) (Serrano L., Advances in Protein Chemistry 53:49-85 (2000)).

Independently from the quantity of the three-dimensional structure differences of peptide bonds, it is often an advantage to support the process of the production of biomolecules (proteins, polypeptides or oligopeptides) having the desired properties by the participation of the most varied folding helpers (e.g.: Stoller et al., 1995, EMBO J. 14:4939-4949; Buchner J., 1999, Trends in Bioch. Sciences 24:136-141; Mayer M. et al., 2000, J. Biol. Chem. 275:29421-29425; Schiene-Fischer C. and Yu C., 2001, FEBS Letters 495:1-6).

By the provision of a new kind of folding helper catalysis, the one that e.g. is realised in the active centre of the APIases, the repertory that is available to the biotechnologist for the economical production of biomolecules by means of the use of folding helpers can be supplemented. In this context, the folding helper catalysis is carried out by either APIases or their variants or by low-molecular mimetics of the APIases produced chemosynthetically. In this context, it can be an advantage for carrying out the biotechnological process to use the very different folding helpers in solution or in a matrix-bound manner at the same time, in consecutive steps or, however, separately in compartments. The biotechnological process of the economical production of particular biomolecules with participation of folding helpers can—this is known to the person skilled in the art—can be carried out in vitro but also in vivo. Contrary to the process taking place in vitro, during carrying out of the process in vivo, biotechnologically modified cells containing the amount of folding helper(s) necessary for the catalysis of the folding process are used.

EXAMPLE 1

The Rate of the Cis/Trans Isomerisation of the Peptide Bond of the Substrate Ala-Leu can be Accelerated by the Protein DnaK The peptide bond of the substrate Ala-Leu is to about 99% in the trans conformation at pH 7.4. An increase of the proton concentration of the aqueous Ala-Leu solution to about 100 mM results in a shift of the equilibrium of the conformations to a higher content of the peptide with the cis conformation. This shift can be measured in the range of 2220-228 nm spectroscopically, since, at this wavelength, the conformation isomer with the cis conformation exhibits a lower extinction coefficient than the conformation isomer with the trans conformation. The isomerisation rate can be measured when the substrate is subjected to a pH modification that has an influence on the cis/trans equilibrium of the substrate and when the rate of the pH modification is higher than the isomerisation rate of the substrate. In this context, the isomerisation rate corresponds to the sum of the individual rates cis to trans and trans to cis of the two conformation isomers of the substrate. In the present example, a so-called Stopped-Flow device from the company Applied Photophysics Ltd. (England) is used. This spectroscopic device makes a rapid mixture of two components and, subsequently, a collection of spectroscopic data, which is rapid and time-independent, possible. Moreover, an accompanying software makes it possible for the rate constants ($k_{obs}$) to be calculated while assuming a concentration/time law that corresponds to a so-called "first-order time law". For the detection of the catalysis, the following assay was selected:

Stock solution Ala-Leu (Bachem, Switzerland) 10 mM dissolved in Aqua dest. with pH 2.0, adjusted by means of HCl Buffer solution: 12.5 mM Tris, 50 mM KCl, 11 mM $MgCl_2$ with HCl adjusted to pH 8.8 DnaK (SIGMA-ALDRICH CHEMIE GmbH, Germany), or produced in a molecular biological way After mixing the components in the Stopped-Flow device, the reaction solution had the following concentrations: 1.66 mM Ala-Leu, 10.4 mM Tris, 41.6 mM KCl, 9.2 mM $MgCl_2$. The pH was 7.6. All the solutions were kept constant at a temperature of 25° C.

FIG. 1 shows a typical picture. The lower curve which shows absorption after about 20 seconds only, which corresponds to the cis/trans equilibrium of the substrate at pH 7.6, was obtained without adding DnaK.

The upper curve which shows a stronger curvature than the lower curve corresponds to the data obtained by a concentration of 624 nM DnaK in the reaction solution. By means of the catalytic effect of 624 nM DnaK, the conformation equilibrium occurs after less than 10 seconds already. By using the analysing software, a corresponding rate constant ($k_{obs}$) can be calculated when assuming a time law of "first order". The non-catalysed reaction results in a constant of $0.36\ s^{-1}$ and the catalysed reaction in a constant of $0.55\ s^{-1}$. The deviation of the calculated measuring points of the calculated curve, solid line in FIG. 1, compared to the values measured individually, can be seen from the values noted below (residuals versus time(s)). The statistic variation of the absolute deviation across the measurement time period proves the quality of the non-linear regression carried out for the determination of the rate constants.

EXAMPLE 2

Figure 2:
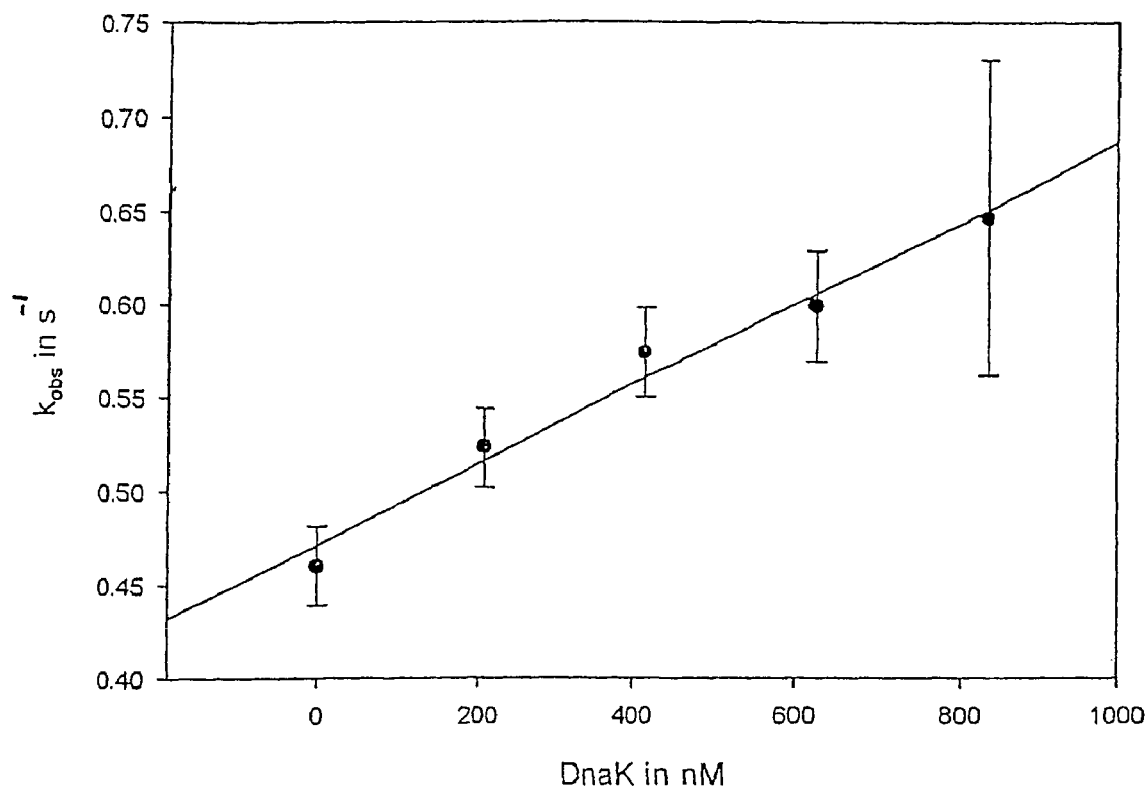
FIG. 2 is a graph representing the dependency of the rate ($k_{obs}$) of cis/trans isomerisation of the substrate Ala-Leu on the concentration of DnaK.

The APIase Catalysis of the Cis/Trans Isomerisation of a Peptide Bond Dependes on the APIase Concentration Used A measurable dose-effect relation is an essential characteristic of chemical catalysts. In the case of dependency on a change of the concentration of the catalyst, said dependency is to be observed when using catalytic amounts. Dependency of that kind is illustrated in FIG. 2 for the catalysis of the cis/trans isomerisation rate of the peptide bond of the dipeptide Ala-Leu by means of the addition of various amounts of DnaK to the measuring solution.

The measurements were carried out by means of the measurement device stated in Example 1. The thickness of the coating of the silica cuvets was 2 mm, the measuring wave length was 220 nm.

The following solutions were used:
Buffer solution: 12.5 mM Tris, 50 mM KCl, 11 mM $MgCl_2$.
Substrate solution: 20 mM Ala-Leu, dissolved in Aqua dest. at pH 2.0.
DnaK stock solution: 20 µM in buffer solution a 4 solutions for use d1, d2, d3 and d4 were produced from the solutions a and c in such a way that, after mixing of one solution for use with solution c each, the following DnaK concentrations were obtained in the cuvet: 0, 208, 416, 625 and 833 nM Due to this mixture, the substrate always had a concentration of 3.33 mM. The pH of the solution in the cuvet was 7.3 each. The error lines indicated result from three independent measurements for the determination of the rate constant $k_{obs}$ with a DnaK concentration.

Figure 3:
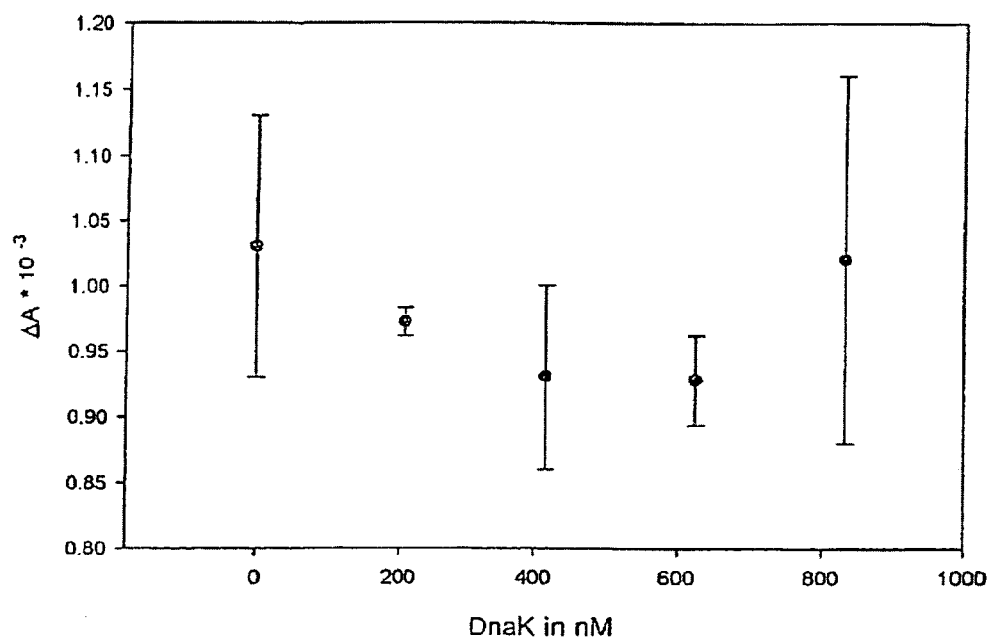
FIG. 3 is a graph representing dependency of the size of the difference in measurement (amplitudes) between absorption at the time t=0 and absorption after adjustment of the cis/trans equilibrium, plotted at different Dnak concentrations

FIG. 3 shows the differences of the absorption resulting from the measurements, straight after start of the reaction and the absorption; the obtained after new adjustment of the cis/trans isomer equilibrium is applied.

EXAMPLE 3

Figure 4:
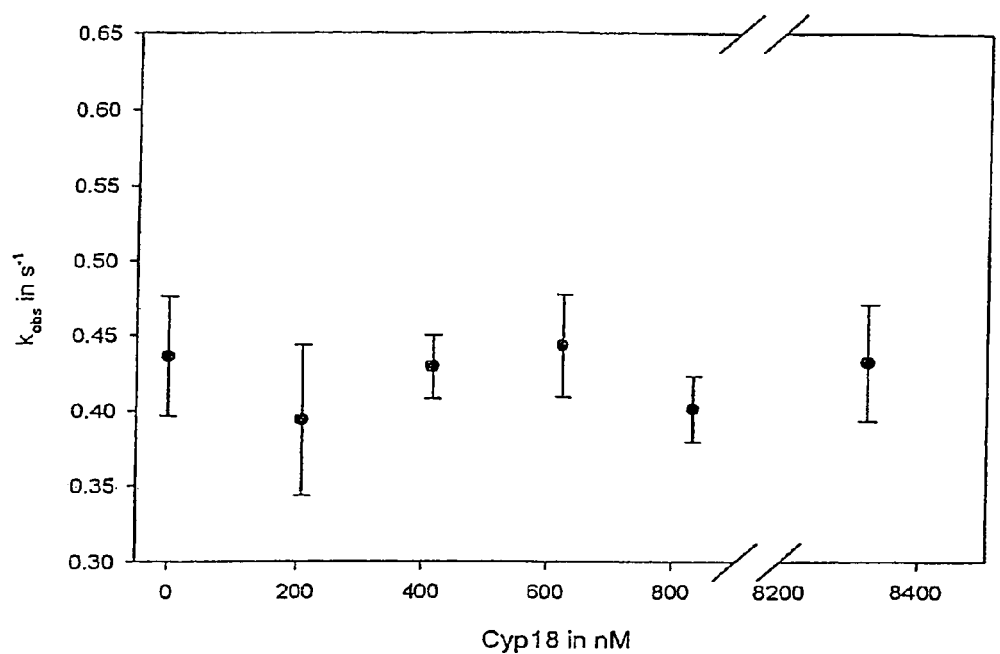
FIG. 4 is a graph representing the dependency of the rate constant of the cis/trans isomerisation of the substrate Ala-Leu on the concentration of Cyp18.

The Peptidyl-Prolyl Cis/Trans Isomerase (PPIase) Cyp18 (EC 5.2.1.8; Accession Number: P05092) or the Reference Protein Bovine Serum Albumine has no Detectable APIase Activity The PPIase Cyp18 belonging to the PPIase family of the cyclophilins is the representative of PPIases which, in relation to the most varied members of the PPIase families, seems to be most widely spread with regard to phylogenetics (Maruyama T. and Furutani M., 2000, Frontiers in Bioscience 5:D821-D836). The substrate specificity of this cyclophilin compared to peptide substrates of PPIases covers a broad range. In this respect, Cyp18 also catalyses the cis/trans isomerisation of phosphorylated Ser-Pro and Thr-Pro peptide bonds (Metzner M. et al, J. Biol. Che. 276:13524-13529 (2001); Schutkowski M. et al., Biochemistry 37:5566-5575 (1998)). In order to establish whether Cyp18 catalyses the cis/trans isomerisation of the dipeptide Ala-Leu, the isomerisation rate was analysed in the presence of up to 8.4 µM Cyp18:

Human Cyp18 was either bought (SIGMA-ALDRICH CHEMIE GmbH, Germany) or produced as recombinant enzyme (E. coli cultures). The cyclophilin concentration of the cyclophilin stock solution of 1.14 mM was determined by means of titration against the cyclophilin inhibitor cyclosporin A (SIGMA-ALDRICH CHEMIE GmbH, Germany). The substrate Ala-Leu (BACHEM, Switzerland) used was produced as 10 mM stock solution in water with a pH of 2.0. The buffer solution used contained a mixture of the following chemicals: 12 mM Tris, 50 mM KCl, 11 mM $MgCl_2$ and was adjusted with HCl to a pH of 8.8. The measurement of the isomerisation rate of the substrate took place with the Stopped-Flow-Photometer (Applied Photophysics Ltd., England) at 25°C. with 228 nm using 1 cm quartz cuvets. By adding the substrate to the mixture of buffer and Cyp18, solutions were produced in the cuvet with Cyp18 concentrations of 0, 208, 416, 625, 833 and 8,330 nM and 1.66 mM Ala-Leu each with a pH of 7.9. Over an observation period of 20 seconds, with a dissolution <0.05 seconds and a mixing time <0.1 second, no acceleration of the cis to trans reaction could be observed (FIG. 4). Independently from the Cyp18 concentration used, the rate constants $k_{obs}$ established are within a range of about $0.43 \pm 0.03$ $s^{-1}$.

In a further experiment, purified bovine serum albumin (SIGMA-ALDRICH CHEMIE GmbH, Germany) was used in a concentration of 1 µM instead of Cyp18. For the purification of the bovine serum albumin, ion exchange and affinity materials were used. Just like Cyp18, bovine serum albumin was not able to catalyse the cis/trans isomerisation of the dipeptide.

The amplitudes of the measured signals, i.e. the difference of the absorption measured straight after the mixing together of all the solutions and the absorption measured after the end of the reaction observed constitute a measure of the quality of the measured values obtained. The non-catalysed cis/trans isomerisation of the substrate Ala-Leu reaches the equilibrium within 20 seconds under the measuring conditions selected.

Figure 5:
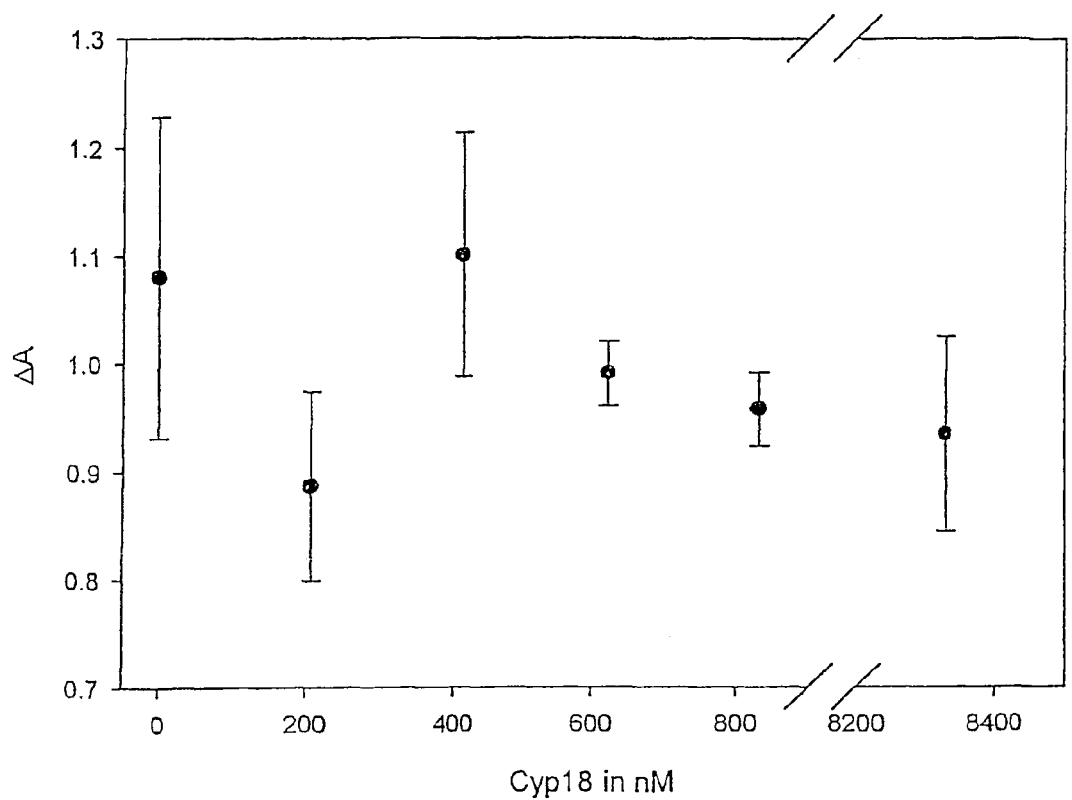
FIG. 5 is a graph representing the size of the difference in measurement (amplitudes) between absorption at the time t=0 and adsorption after adjustment of the cis/trans equilibrium, plotted at different Cyp18 concentrations.

The absorption difference of the amplitudes is about $1.0 \pm 0.2 \times 10^{-3}$. As can be seen from FIG. 5, the obtained absorption differences of the measurements summarized in FIG. 4 are independent from the Cyp18 concentration.

EXAMPLE 4

The Protein DnaK has APIase, but No PPIase Activity

As can be seen from Example 3, it is not possible to catalyse the cis/trans isomerisation of a peptide bond in a dipeptide composed of amino acids by means of catalytic amounts of the PPIase cyclophilin. According to the invention, said catalysis is successful with substances having APIase activity. As is shown below, the APIase activity of the APIase DnaK is specific and excludes the catalysis of the cis/trans isomerisation of prolyl-peptide bonds.

For the detection of a PPIase catalysis, there are numerous methods (e.g.: Fischer, G. (1994), Angew. Chemie Intl. ed Engl. 33, 1415-1436). The detection methods most commonly used include the isomer-specific hydrolysis. This method takes advantage of the regio-specificity of different proteases such as chymotrypsin or subtilisin with respect to protease cleavage sites located in P2' position to the prolyl-peptide bond (Fischer, G., Bang, H. & Mech, C., 1984, Biomed. Biochim. Acta, 43:1101-1111).

The details of Example 5 are described as follows:
Measuring device: Spectrophotometer Diodenarray HP8452A (Hewlett Packard, USA)

Substrate: Suc-Ala-Phe-Pro-Phe-NHNp (SEQ ID NO:2) (BACHEM, Switzerland)
Protease: Chymotrypsin (Merck, Germany)
Measure temperature: 10° C.
Buffer: 35 mM Hepes, pH 7.8
Protease solution for use: 5 mg protease per ml buffer
Substrate solution for use: 35 mg substrate dissolved in 1 ml DMSO
DnaK solution for use: 30 µM in buffer
Cuvet: 1 ml quartz cuvet, thickness of layer 1 cm
Measuring wave length: 390 nm
Process: After attemperating a mixture of substrate, DnaK and buffer, the reaction is started by rapid addition and homogenous distribution of the protease solution for use. In this way, a chymotrypsin concentration of 0.83 mg/ml is achieved in the cuvet. By means of the substrate amount contained in the cuvet, a final extinction of about 0.43 is accomplished after complete turnover of the substrate. The concentrations of DnaK contained in the cuvet were 0.250 and 1,000 nM.

Figure 6:
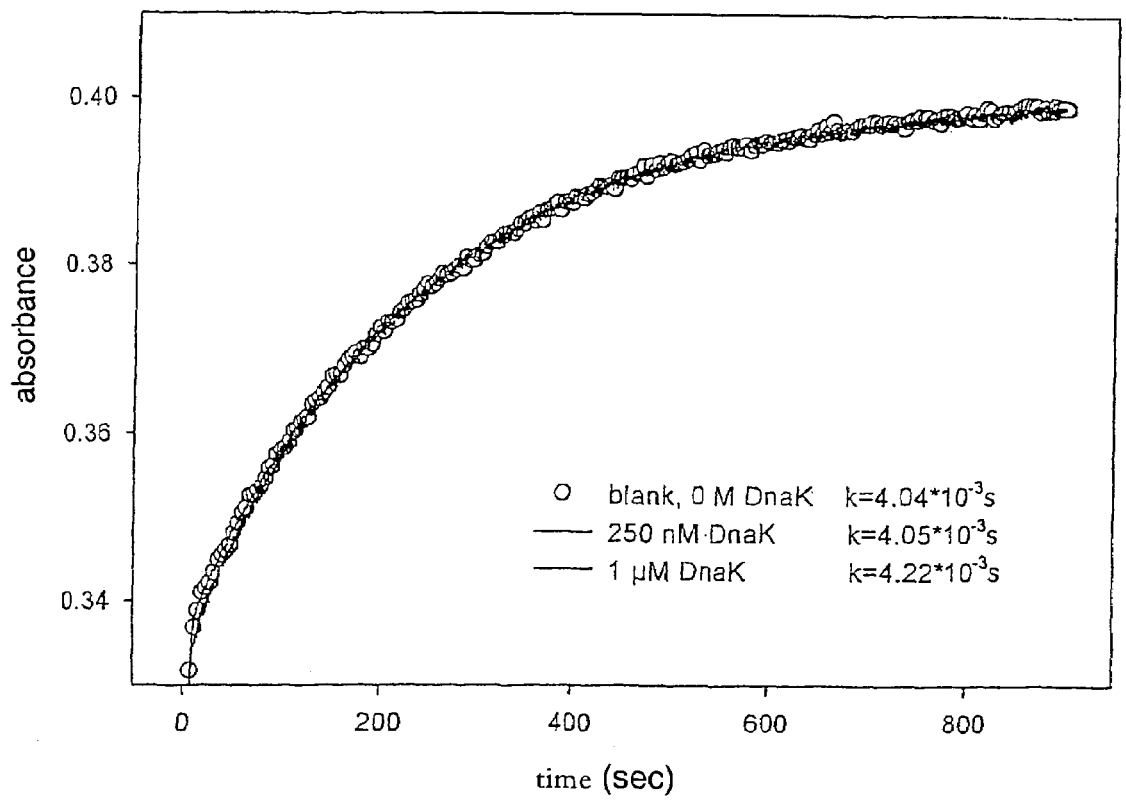
FIG. 6 is a graph representing the peptidyl-prolyl cic/trans isomerisation rate of the substrate Suc-Ala-Phe-Pro-Phe-NHNp (SEQ ID NO:2) by means of isomer-specific proteolysis over a period of time and measured using different amounts of Dnak.

Result: DnaK did not show a visible influence on the cis/trans isomerisation rate of the substrate. In the error range, the calculated rate constants $k_{obs}$ of the cis/trans isomerisation of the substrate showed no deviation as to the rate constant which was obtained without DnaK (blank). FIG. 6 shows the measured values of the three measuring series on top of one another. The circles relate to the measurement without DnaK and the points to the measurements with addition of DnaK.

EXAMPLE 5

Screening of Peptide Libraries

Since the binding of molecules to a corresponding target enzyme provides a first indication as to the possibility of finding an inhibitor and peptide libraries make it possible to find such potential inhibitors, a corresponding library (Z. Songyang et al., 1993, Cell 72:767) was used. When using all the natural amino acids with the exception of cysteine, when using equimolar amounts in each degenerated position, theoretically, $19^6=4.7 \times 10^7$ different peptide sequences are produced for two libraries. For coupling of the APIase DnaK, an activated agarose (Affi-Gel 10, BIO-RAD Laboratories Munich) was used as matrix according to the manufacturer's instructions. After incubation of the peptide mixture obtained from the library with the DnaK sepharose and extensive washing of the DnaK gel with 1 mM ammonium acetate buffer (pH 7.4), bound peptides can be eluted with 30% acetic acid and sequenced. The peptide sequences found which bind to DnaK can be synthesised conventionally in mg amounts and be validated by means of mass spectrometry and NMR. For assessment of the inhibition of such a peptide compared to the APIase activity of DnaK, the peptide has to be added to the activity assay described in Example 1. The concentration of peptide sufficient to inhibit the APIase activity by 50% ($IC_{50}$ value) is used to compare the inhibitory valency of individual inhibitors.

EXAMPLE 6

The APIase Activity of DnaK can be Inhibited by Naturally Occurring Peptides The $IC_{50}$ values (Example 5) of peptide sequences obtained, which inhibit the APIase activity, can be compared to natural peptide sequences about which there has already been knowledge in the scientific literature. Such knowledge is available to the person skilled in the art by means of literature search in literature data banks (e.g.: MEDLINE, CURRENT CONTENTS) but also by keeping track of technical literature or patent libraries (e.g.: DELPHION). Individual data obtained by means of peptide libraries and verified by APIase activity tests indicate that the peptide sequence (-Arg-Pro-Lys-Pro-Gln-Gln-Phe-Phe-Gly-Leu-Met-) (SEQ ID NO:3) occurring in the peptide hormone substance P (e.g. Jessell T M., 1982, Nature 295:551) should be suitable for inhibiting the APIase activity of DnaK.

Figure 7:
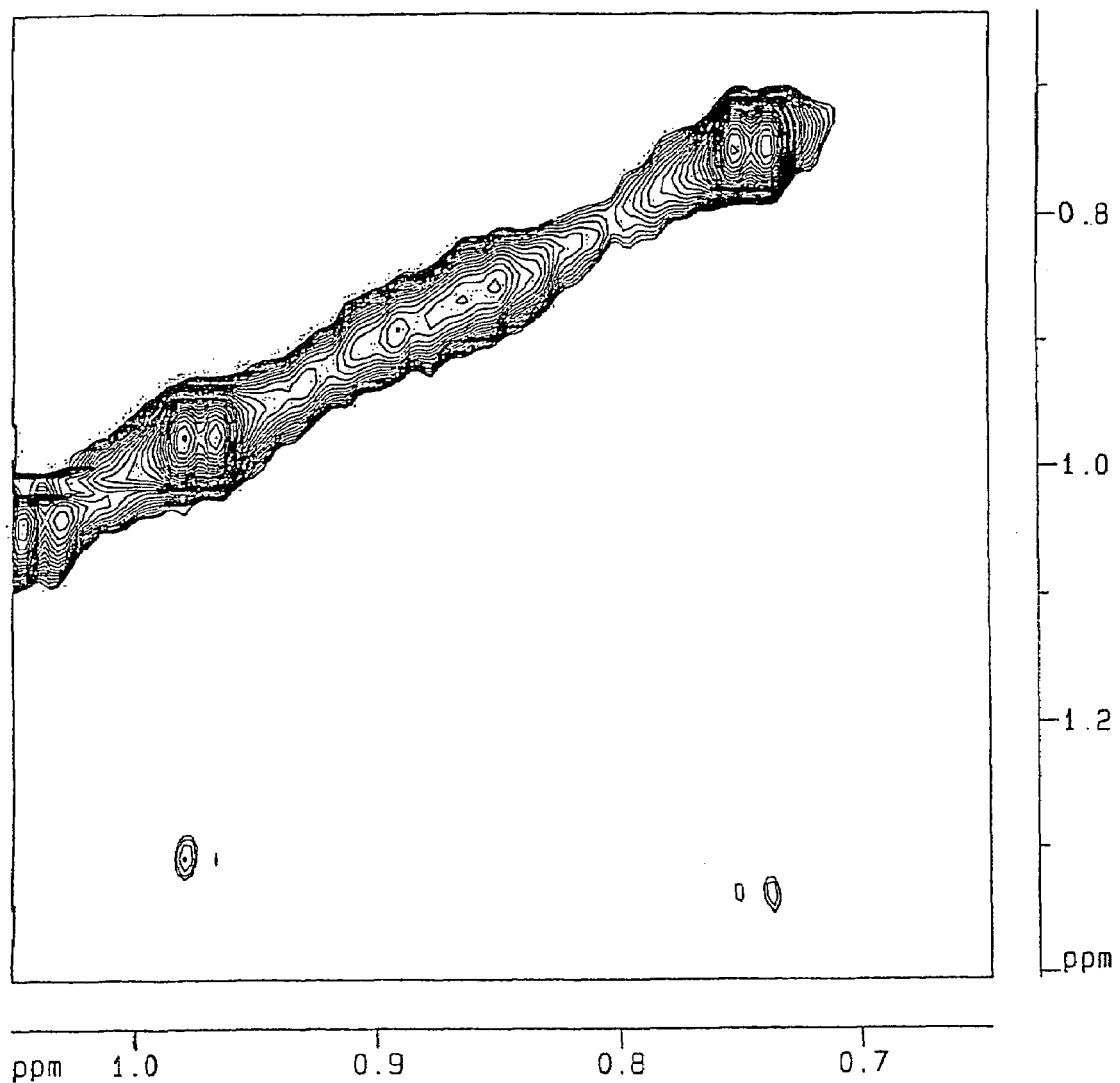
FIG. 7 is a plot showing the alanine-methyl region of a 2D exchange $^1$H NMR-spectrum for the substrate Ala-Ala-Tyr-Ala-Ala (SEQ ID NO:1).

In order to test that, substance P (BACHEM Biochemica GmbH, Heidelberg) was subjected to the spectrophotometric activity test of the APIase activity of DnaK (Example 1) in increasing concentrations 1 to 100 µM. From the dose-effect curve (FIG. 7) of the inhibition of the APIase activity by substance P, an IC50 value of 76±16 µM can be obtained.

EXAMPLE 7

In Homogenates of Biological Samples Proteins with APIase Activity Exist

In order to find potential proteins with APIase activity, biological samples of the microorganism Escherichia coli (E. coli) and of a mammal (domestic pig) were used. E. coli homogenate: After transfer into a suspension culture, the bacteria were kept in a shake flask according to the standard instructions at 30° C. and the increase of the cell mass was observed by spectroscopic measuring of the cell density. Straight after accomplishment of the logarithmic development phase of the bacteria, the cells were harvested by centrifugation. After two-fold washing of the cells with washing buffer, the cells were destroyed by means of a decrease of pressure (French press). By means of high-powered centrifugation at 80,000 g for 10 minutes, a clear supernatant was obtained.

Homogenate of pig's brain: 10 g of a pig's brain, which was deep-frozen by means of liquid nitrogen straight after it had been taken out, were cut off in small pieces and 1 ml lysine buffer in an ice bath were added. After careful mincing of the sample by means of shear forces (Elvejheim-Potter, Netherlands) and centrifugation at 80,000 g for 20 minutes, a clear fraction in the middle could be obtained after discarding of an upper inhomogeneous supernatant.

Both the supernatant (A) obtained from bacteria and the fraction (B) obtained from pig's brain were subjected to the activity test described in Example 1. Dilutions of both supernatants were able to significantly accelerate the cis/trans isomerisation of the substrate Ala-Leu. Heating of both supernatants to 70° C. for 30 minutes led to the complete inactivation of the accelerating activity.

By means of carrying out several purification steps and using the MALDI mass spectrometry, the DnaK mentioned in Example 1 could be identified from an active fraction of the E. coli supernatant (A) as the protein exhibiting APIase activity.

EXAMPLE 8

Detection of the Cis/Trans Isomerisation of a Single Peptide Bond of a Pentapeptide and the Catalysis of the Isomerisation by the APIase Activity of the Protein DnaK by Means of NMR Measurement Apart from the determination of the cis/trans isomerisation of secondary amide peptide bonds by means of UV-VIS measurements, as described in the above Examples, the isomerisation of this peptide bond can be measured by other methods, too, as is proven by numerous publications. Thus, e.g. the rate of the cis/trans isomerisation of the dipeptide Gly-Gly could be determined by means of the Raman spectrum at 206 nm (Li P. et al., JACS (1997) 119:1116-11120). With detailed knowledge of the three-dimensional structure and with specific spectroscopic characteristics being present, the cis/trans isomerisation rate of individual secondary amide peptide bonds can be determined in proteins or oligopeptides by means of spectroscopic methods. The determination of the cis/trans isomerisation rate of the Tyr38-Ala39 bond in the protein Rnase $T_1$ is well examined (Odefey C. et al., 1995, J. Mol. Biol. 245:69-78; Mayr L. et al., 1994, J. Mol. Biol. (1994) 240:288-293; Dodge R W. et al., 1996, Biochemistry 35:1548-1559).

A further possibility, only described in 1998, is the determination of the cis/trans isomerisation rate of secondary amide peptide bonds containing aromatic amino acids by means of 2D 1H NMR exchange experiments (Scherer G. et al., 1998, JACS 120:5568-5574). In Example 8, this NMR method is used to determine a catalytic acceleration of the cis/trans isomerisation of the peptide bonds Ala-Tyr and Tyr-Ala within the pentapeptide Ala-Ala-Tyr-Ala-Ala. The acceleration is accomplished by catalytic amounts of DnaK.

Material and Method:

NMR Device: Bruker DRX-500, Equipped with z-gradient

Figure 8:
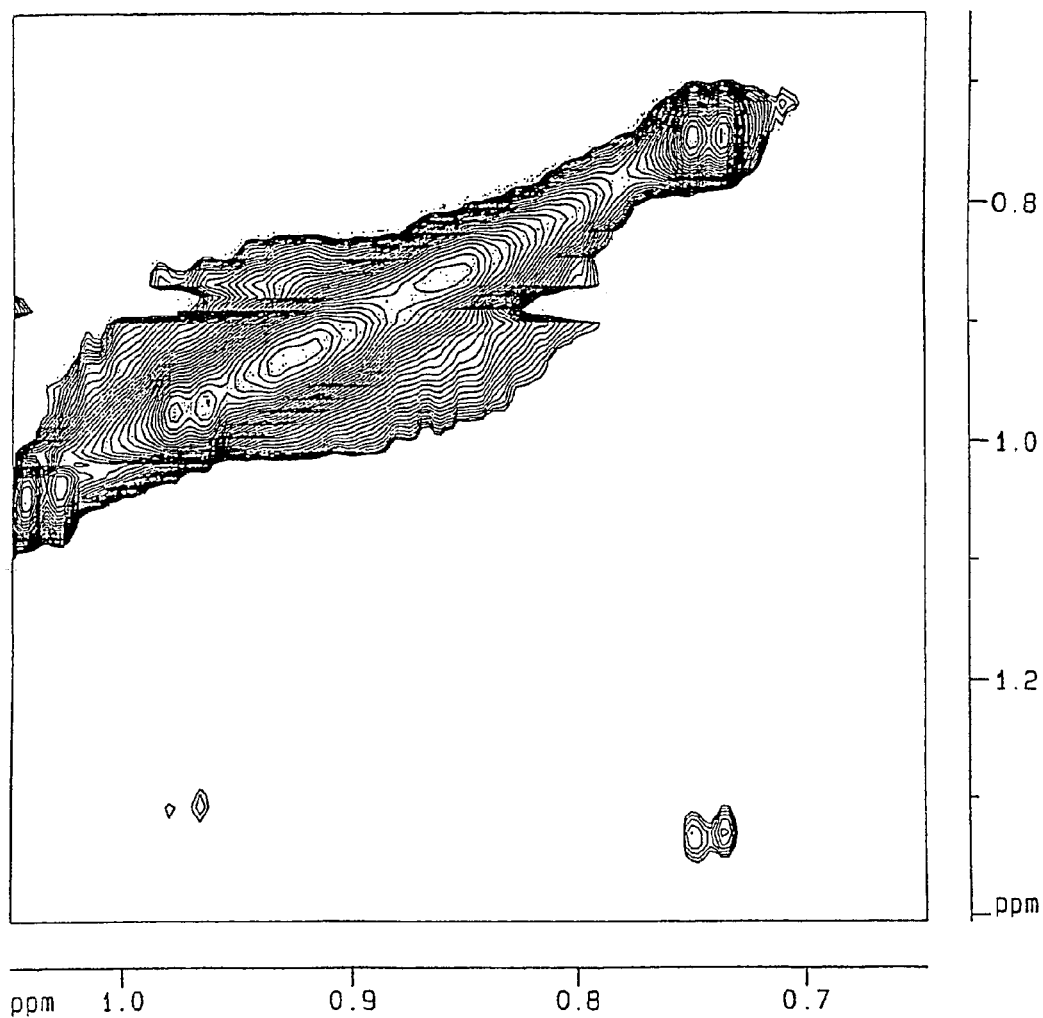
FIG. 8 is a plot showing the alanine-methyl region of a 2D exchange $^1$H NMR-spectrum for the substrate Ala-Ala-Tyr-Ala-Ala (SEQ ID NO:1) following addition of catalytic amounts of APIase.

FIG. 8: The alanine methyl region from the two-dimensional exchange 1H-NMR spectrum of 25 mM Ala-Ala-Tyr-Ala-Ala in 25 mM Tris, 11 mM $MgCl_2$, 50 mM KCl, 9:1$H_2O$:$D_2O$, pH 7.1 at 278° K. The mixing time of the phase-sensitive NOESY was 330 ms. Each FID had 184 scans. The amount of data from $t_1 \times t_2$=512×8192 points covered a spectral range of 5501 Hz×5482 Hz. The correction of the base line was carried out by adjustment with a polynom of fifth order in the $F_2$ dimension. The intensities of the spectrum, i.e. the levels in the two-dimensional illustration, were normed to a cross signal which is independent from the peptide structure and which has a comparable intensity, that is the cross signal caused by the chemical exchange between the two $^{13}C$-satellites of $^1Ala$.

Figure 9:
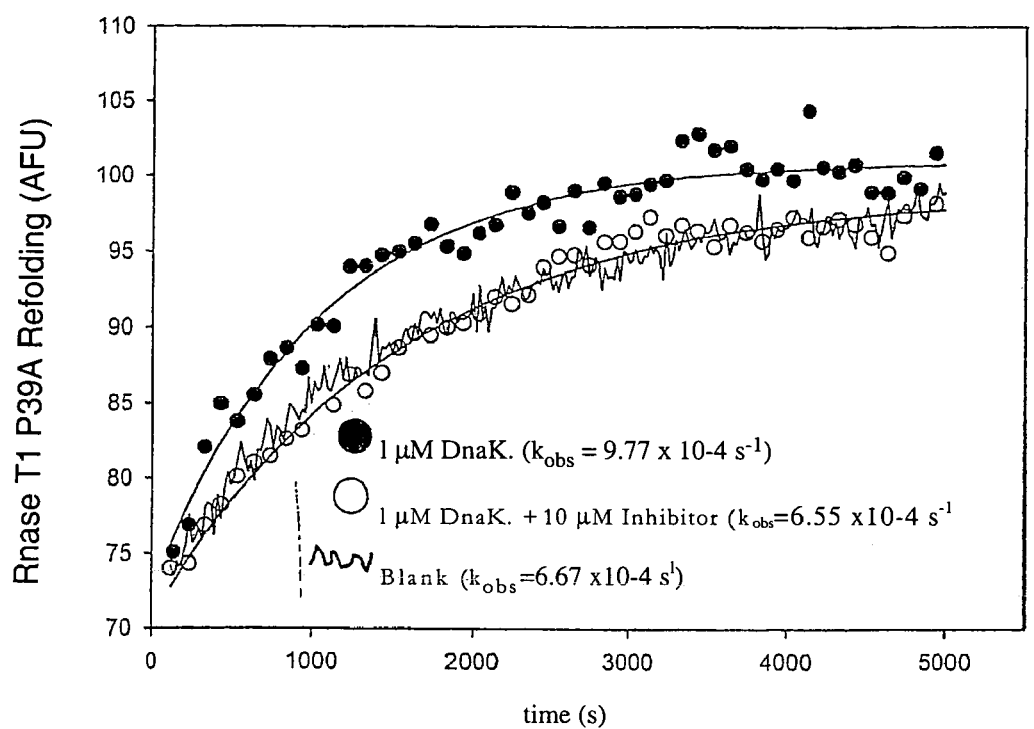
FIG. 9 is a graph representing the foldback of RNAse T1 P39A over time measured in the presence of DnaseK, DnaseK and 37/B10 inhibitor, or alone.

FIG. 9: The same section from the two-dimensional exchange $^1H$-NMR spectrum of 25 mM Ala-Ala-Tyr-Ala-Ala in 25 mM Tris, 11 mM $MgCl_2$, 50 mM KCl, 9:1$H_2O$:$D_2O$, pH 7.1 at 278° K as in FIG. 7. The experiment was carried out under identical conditions as described above. In addition, 20 µM DnaK was contained in the measuring solution.

Result: The aromatic amino acid tyrosine is flanked by two alanines in the pentapeptide. The CH3 signals of the two alanines corresponding to the cis confirmation can be localised in the two-dimensional NOESY experiment by means of the Cross Peaks at 0.74 ppm and 0.97 ppm. The corresponding signals for the trans confirmation are found at 1.33 ppm and 1.31 ppm (not shown in the FIGS.). The chemical shifts correspond to the shifts which were determined for the CH3-alanin signals of Tyr-Ala (0.33 ppm) and Ala-Tyr (0.57 ppm) (Scherer et al. 1998). From the form of the 1H NMR signals and their sensible change with change of the isomerisation rate, the cis/trans isomerisation rates can be calculated by means of mathematical methods. In this context, a broadening of the 1H NMR signals corresponds to the increase of the isomerisation rate. As FIG. 8 shows, when the two cross signals are compared, it is mainly the cross signal corresponding to the Ala-Tyr peptide bond that broadens under the influence of catalytic amounts of DnaK. This means that the APIase activity of the DnaK exhibits a distinct substrate specificity. In the pentapeptide substrate Ala-Ala-Tyr-Ala-Ala, the cis/trans isomerisation of the Ala-Tyr peptide bond is catalysed in a better way than the one of the Tyr-Ala peptide bond.

EXAMPLE 9

Quantification of APIase Activity Measuring by Means of NMR

In a further analysis of the method of the two-dimensional NOESY experiment illustrated in Example 8, the cross signals can be quantified by means of common mathematical techniques. By using relative intensities related to a cross signal independent from the peptide structure of comparable intensity (cross signal caused by the chemical exchange between the two $^{13}C$-satellites of $^1Ala$), the influence of most different additions on the rate of the cis/trans isomerisation of the peptide bonds Ala-Tyr and Tyr-Ala in the pentapeptide Ala-Ala-Tyr-Ala-Ala can be determined (Tab. 1).

Tab. 1 Relative intensites of the cross signals of the peptide bonds Ala-Tyr and Tyr-Ala of the pentapeptide Ala-Ala-Tyr-Ala-Ala with dependency from additions. Conditions as stated in Example 8

TAB. 1

Relative intensities of the cross signals of the peptide bonds Ala-Tyr and Tyr-Ala of the pentapeptide Ala-Ala-Tyr-Ala-Ala with dependency from additions. Conditions as stated in Example 8.

| | Ala-Tyr | Tyr-Ala |
|---|---|---|
| no addition | 3.50 ± 0.51 | 3.89 ± 0.32 |
| 20 µM DnaK*[)] | 6.37 ± 0.57 | 3.39 ± 0.45 |
| 20 µM FKBP12*[)] | 3.94 ± 0.87 | 2.68 ± 0.75 |
| 20 µM Parvulin*[)] | 2.90 ± 0.96 | 3.11 ± 0.46 |
| 20 µM trigger factor (TF)*[)] | 3.83 ± 1.07 | 4.42 ± 0.58 |
| 20 µM fragment of the TF*[)] | 3.96 ± 0.77 | 3.22 ± 0.58 |

*[)]All the additives were produced recombinantly or they were bought. Human DnaK and FKBP12 were obtained from SIGMA-ALDRICH GmbH (Germany), Parvulin (Rahfeld et al., 1994, FEBS Letters 352:180-184), trigger factor (Stoller G. et al., 1995, EMBO J. 14:4939-4948) and a fragment of the trigger factor (Stoller G. et al., 1996, FEBS Letters 384:117-122) were aliquots of the proteins produced in the cited studies or they were produced in an analogue manner.

*[)]All the additives were produced recombinantly or they were bought. Human DnaK and FKBP12 were obtained from SIGMA-ALDRICH GmbH (Germany), Parvulin (Rahfeld et al., 1994, FEBS Letters 352:180-184), trigger factor (Stoller G. et al., 1995, EMBO J. 14:4939-4948) and a fragment of the trigger factor (Stoller G. et al., 1996, FEBS Lettters 384:117-122) were aliquots of the proteins produced in the cited studies or they were produced in an analogue manner.

Assessment:

The APIase activity of the APIase DnaK is regio-specific. Whereas the cis/trans isomerisation of the Ala-Tyr peptide bond is accelerated by 20 µM DnaK in such a way that the relative intensity of the cross signal nearly doubles, the concentration of DnaK has no influence on the cis/trans isomerisation rate of the Tyr-Ala peptide bond under the conditions selected.

The peptidyl-prolyl cis/trans isomerases FKBP12, Parvulin and trigger factor or trigger factor fragment neither catalyse the cis/trans isomerisation of the Ala-Tyr peptide bond nor the cis/trans isomerisation of the Tyr-Ala peptide bond of the pentapeptide Ala-Ala-Tyr-Ala-Ala.

EXAMPLE 10

APIase Inhibitors have Antibacterial Properties

As stated in Example 6, the information obtained by peptide libraries and by means of APIase activity test make it possible to find natural, i.e. already known, APIase inhibitors. One of the potential natural APIase inhibitors is the sequence VDKGSYLPRPTPPRPIYNRN (SEQ ID NO:4) which was isolated as antibacterial peptide pyrrhocoricin from insects (Otvos L., 2000, J. Peptide Science 6:497-511), however as a peptide glycosylated at the threonine. Pyrrhocoricin can be produced according to standard methods (solid phase synthesis, Fields G B et al., 1990, Int. J. Pept. Protein Res. 35:161-214). The purification of the peptide can be accomplished by means of RI-IPLC (reversed-phase high-performance liquid chromatography), the validation of the peptide by means of mass spectrometry. The amount of peptide of the lyophilised product can be determined by UV-VIS spectroscopy by means of the peptide bond. By means of the APIase activity assay stated in Example 1, the inhibition of the APIase activity of DnaK can be determined by the peptide pyrrhocoricin. Despite the fact that the peptide, in contrary to the compound isolated from insects, is not glycosylated, it inhibits the APIase activity of the DnaK. The antibacterial activity of the APIase inhibitor can, as described in Hoffmann et al. (1999, Biochim. Biophys. Acta 1426:459-467), be carried out against cultivated bacteria. Against the *Escherichia coli* stem D22, an $IC_{50}$ value of 150 nM can be determined for this substance.

EXAMPLE 11

Measuring of the Effect of APIase Inhibitors on the Pathogenetic Folding of Prion Protein The difference between natural prion protein $PrP^c$ and the "wrongly" folded scrapie prion protein $PrP^{Sc}$ which is pathogenetic or characteristic for the disease can be determined by means of commercial assays, as e.g. by means of the different hydrolysis stability of the two proteins (e.g. Bueler H. et al., 1994, Mol. Med. 1:19-30).

The conversion from $PrP^C$ to $PrP^{Sc}$ is accomplished
a) by incubation of a 1,000-fold dilution of brain homogenates of hamsters which are infected with scrapie, i.e. for which $PrP^{Sc}$ proteins can be determined in brain homogenates clearly and in a great amount with
b) 5% brain homogenate of healthy hamsters and
c) by effect of ultrasound, as described in Saborio G P. et al., (2001, Nature 411:810-813).

After 10 to 20 ultrasound cycles, the increase of $PrP^{Sc}$ in the incubation solution can be clearly determined in the immunoblot as difference to the control (incubation cycles without ultrasound). By addition of a mixture of APIase inhibitors to such a $PrP^C$-$PrP^{Sc}$ conversion solution, their effect as active agent can be quantified for the inhibition of the conversion of $PrP^C$ into $PrP^{SC}$. Such active agents are e.g. cyclic tetrapyrroles (such as prophyrins and phthalocyanines; Priola S A. et al., 2000, Science, 287:1503-1506) but also oligopeptides such as e.g. the sequence AAAAGAVVGGLGGYMLG-SAMSRPMMIHV (SEQ ID NO:5) derived from the prion (Chabry J. et al., 1998, J. Biol. Chem. 273:13203-13207).

EXAMPLE 12

APIase Catalyses the Foldback of a Protein with a Cis Peptide Bond

Figure 10:
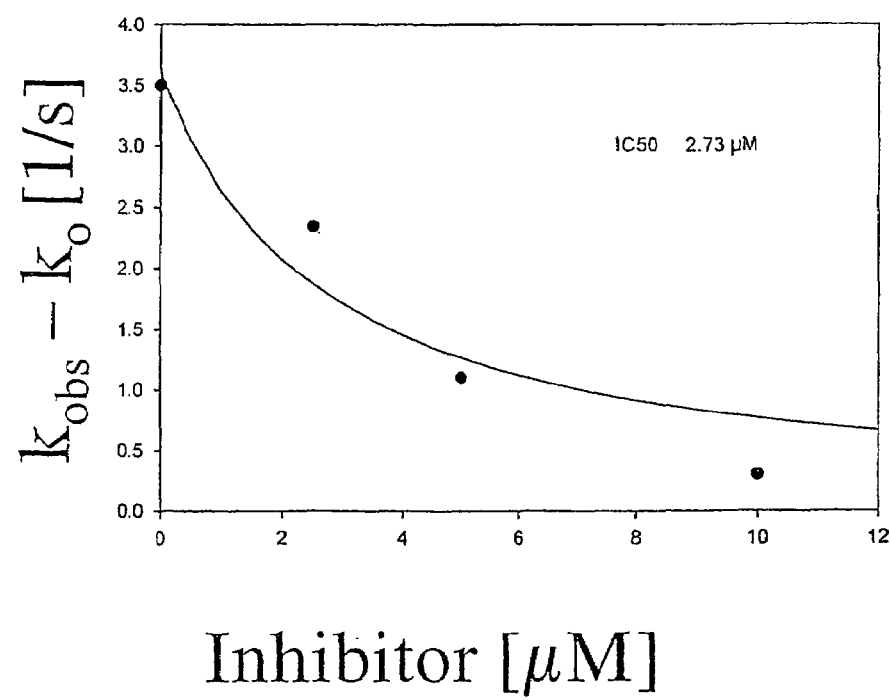
FIG. 10 is a graph representing the foldback rate of RNAse T1 P39A measured at different 37/B10 inhibitor concentrations.

RNAse T1 contains a Ser-Pro sequence with a cis conformation at the sequence site 38/39. Foldback experiments with RNAse T1 show that the foldback rate is influenced by the conformation of this peptide sequence. In detail, the protein is unfolded by suitable additives and the renaturation rate is measured and registered after removal of the additives, e.g. by rapid dilution. As is shown (Scholz et al., Biol. chem. 1998, March; 379(3): 361-5), the exchange of the prolin 39 with an alanine (P39A) leads to a protein mutant whose foldback rate is further influenced by this peptide bond. Added APIase, dependent on concentration, catalyses the isomerisation of this non-prolyl peptide bond and, thus, the foldback of the P39A mutant. Such a foldback experiment as described in Scholz et al., Biol. Chem. 1998, 379(3):361-365, is shown in FIG. 9. Whereas the foldback rate exhibits a rate constant of $6.67 \times 10^{-4 \cdot s}$ without APIase addition, an acceleration to $9.77 \times 10^{-4 \cdot s}$ is observed with addition of 1 µM DnaK. The addition of 10 µM inhibitor 37/B10 causes such an inhibition that the foldback rate corresponds to the rate measured without inhibitor. From the plotting of the rates of the foldback measured at different inhibitor concentrations, as shown in FIG. 10, the efficiency of the inhibitor e.g. as IC50 can be determined.

Assay Approach:

28 mM RNAse T1 P39A was incubated with 5 M guanidinium-Cl and 0.1 M Tris-HCl at pH 8 at 15° C. for 60 min. The foldback at 15° C. was started by a 40-fold dilution of the unfolded protein in foldback buffer (0.1 Tris-HCl, 50 mM KCl, 11 mM $MgCl_2$) at pH 8. The foldback was determined as increase of the protein fluorescence at 320 nm (10 nm width of band) with excitation of 278 nm (1.5 nm width of band) with a Jobin-Yvon-Spex Fluoromax-2 fluorescence spectrometer.

Other IC50 values, too, were determined in the same manner, as listed in the table below.

| substance | IC50 [µM] |
| --- | --- |
| 37B10 | 2.73 |
| 37/B11 | 5.9 |
| 30/B4 | 7.5 |
| 53/B5 | 26.4 |
| 28/C8 | 55.3 |
| 28/C3 | 74.6 |
| 28/B7 | 177.1 |

The invention claimed is:

1. A pharmaceutical composition comprising a compound selected from the group consisting of:

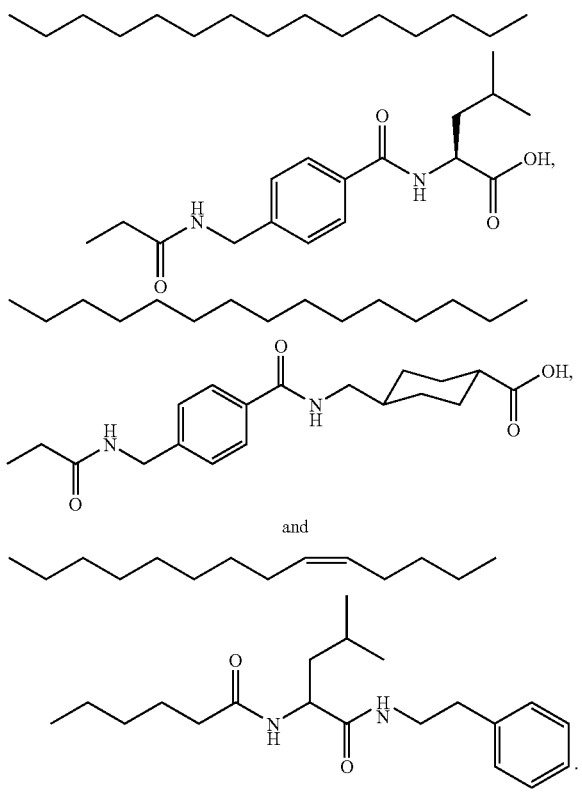

and

2. The pharmaceutical composition according to claim 1 comprising a pharmaceutically acceptable carrier.

3. A compound selected from the group consisting of:

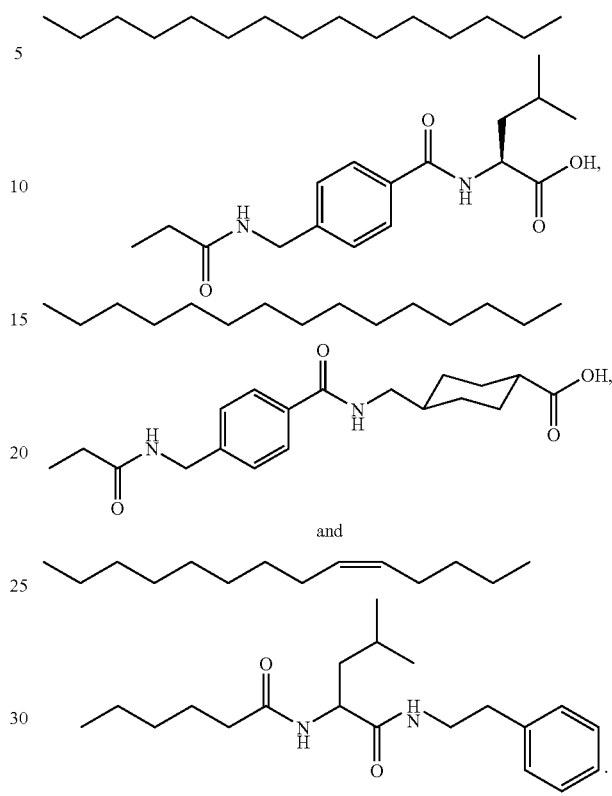

and

4. A method for the preparation of a pharmaceutical composition comprising a step of mixing a compound of claim 3 with a pharmaceutically acceptable carrier.

* * * * *

UNITED STATES PATENT AND TRADEMARK OFFICE
CERTIFICATE OF CORRECTION

PATENT NO. : 7,589,065 B2 Page 1 of 1
APPLICATION NO. : 10/487750
DATED : September 15, 2009
INVENTOR(S) : Schiene-Fischer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1099 days.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

PATENT NO.        : 7,589,065 B2                              Page 1 of 2
APPLICATION NO. : 10/487750
DATED             : September 15, 2009
INVENTOR(S)       : Cordelia Schiene-Fischer et al.

It is certified that error appears in the above-identified patent and that said Letters Patent is hereby corrected as shown below:

Title page, left column, under "Inventors"
Third Inventor Down, City "Richen" should be --Riehen--

Column 31: --should be as illustrated below--

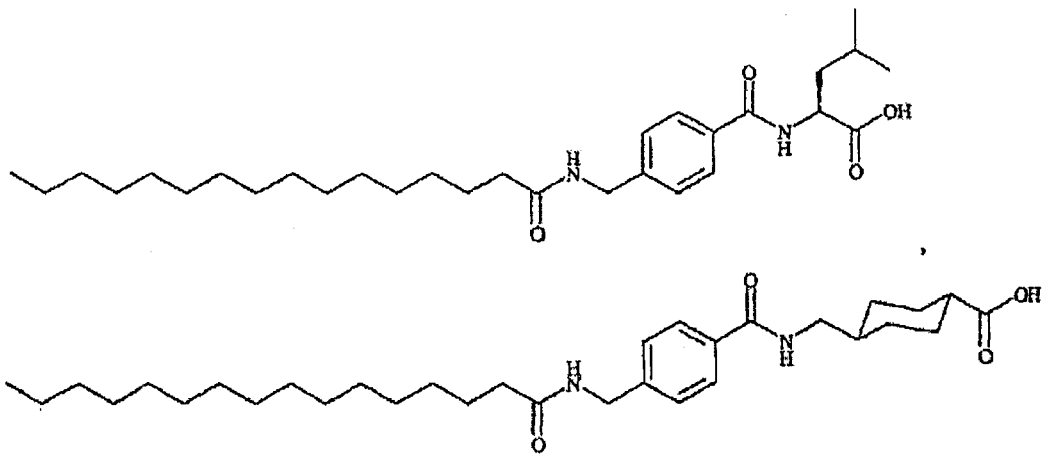

and

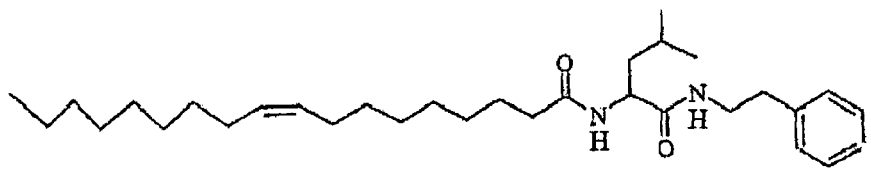

Signed and Sealed this

Twenty-third Day of November, 2010

David J. Kappos
*Director of the United States Patent and Trademark Office*

CERTIFICATE OF CORRECTION (continued)
U.S. Pat. No. 7,589,065 B2

Column 32: --should be as illustrated below--

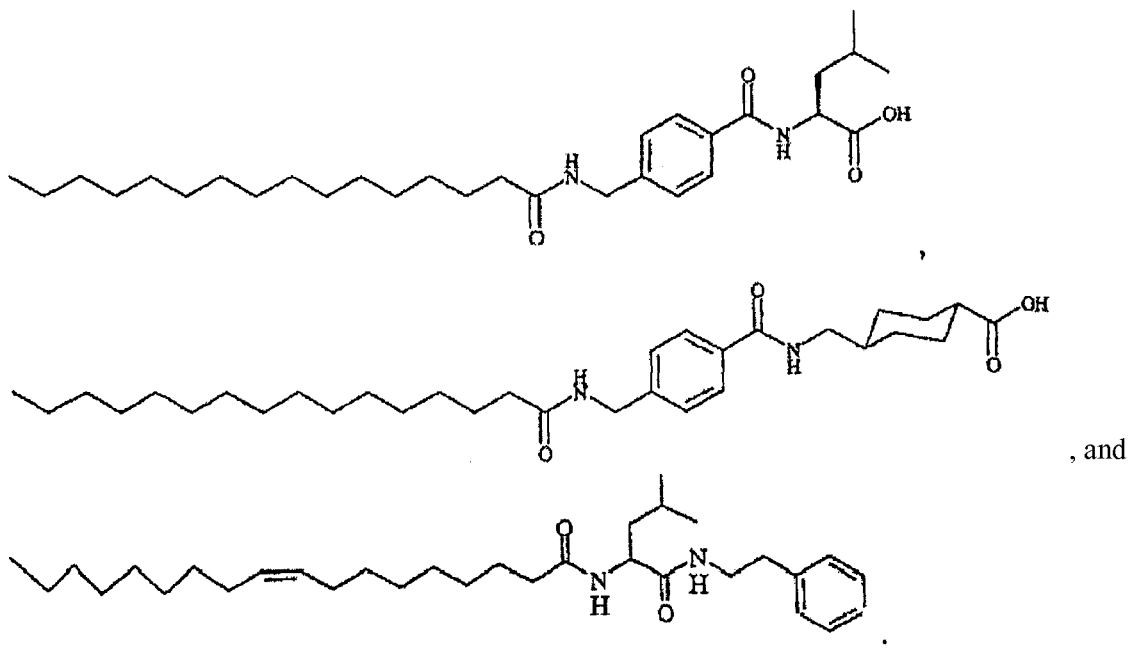

, and

SEQUENCE LISTING

<160> NUMBER OF SEQ ID NOS: 5

<210> SEQ ID NO 1
<211> LENGTH: 5
<212> TYPE: PRT
<213> ORGANISM: Artificial
<220> FEATURE:
<223> OTHER INFORMATION: Chemically synthesized peptide fragment

<400> SEQUENCE: 1

Ala Ala Tyr Ala Ala
1               5

<210> SEQ ID NO 2
<211> LENGTH: 4
<212> TYPE: PRT
<213> ORGANISM: Artificial
<220> FEATURE:
<223> OTHER INFORMATION: Chemically synthesized peptide fragment

<400> SEQUENCE: 2

Ala Phe Pro Phe
1

<210> SEQ ID NO 3
<211> LENGTH: 11
<212> TYPE: PRT
<213> ORGANISM: Homo sapiens

<400> SEQUENCE: 3

Arg Pro Lys Pro Gln Gln Phe Phe Gly Leu Met
1               5                   10

<210> SEQ ID NO 4
<211> LENGTH: 20
<212> TYPE: PRT
<213> ORGANISM: Artificial
<220> FEATURE:
<223> OTHER INFORMATION: Chemically synthesized peptide fragment

<400> SEQUENCE: 4

Val Asp Lys Gly Ser Tyr Leu Pro Arg Pro Thr Pro Pro Arg Pro Ile
1               5                   10                  15

Tyr Asn Arg Asn
            20

<210> SEQ ID NO 5
<211> LENGTH: 27
<212> TYPE: PRT
<213> ORGANISM: prion

<400> SEQUENCE: 5

Ala Ala Ala Ala Gly Ala Val Val Gly Gly Leu Gly Gly Tyr Met Leu
1               5                   10                  15

Gly Ser Ala Met Ser Arg Pro Met Met His Val
            20                  25